(12) United States Patent
Harvey

(10) Patent No.: US 9,963,651 B1
(45) Date of Patent: *May 8, 2018

(54) HIGH DENSITY CYCLIC FUELS DERIVED FROM LINEAR SESQUITERPENES

(71) Applicant: The United States of America as Represented by the Secretary of the Navy, Washington, DC (US)

(72) Inventor: Benjamin G Harvey, Ridgecresst, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/291,615

(22) Filed: Oct. 12, 2016

Related U.S. Application Data

(60) Division of application No. 14/314,305, filed on Jun. 25, 2014, now Pat. No. 9,493,717, which is a continuation-in-part of application No. 13/676,541, filed on Nov. 14, 2012, which is a continuation-in-part of application No. 12/511,796, filed on Jul. 29, 2009, now Pat. No. 8,395,007.

(60) Provisional application No. 61/840,322, filed on Jun. 27, 2013, provisional application No. 61/562,681, filed on Nov. 22, 2011.

(51) Int. Cl.
*C07C 2/52* (2006.01)
*C10L 1/04* (2006.01)
*C07C 6/04* (2006.01)
*C07C 5/03* (2006.01)
*C07C 5/27* (2006.01)

(52) U.S. Cl.
CPC .................. *C10L 1/04* (2013.01); *C07C 2/52* (2013.01); *C07C 5/03* (2013.01); *C07C 5/27* (2013.01); *C07C 6/04* (2013.01); *C10L 2200/0469* (2013.01)

(58) Field of Classification Search
CPC ...... C07C 5/31; C07C 2/52; C10L 1/04; B01J 2231/543; B01J 2231/645
USPC .................................. 585/502, 508
See application file for complete search history.

(56) References Cited

U.S. PATENT DOCUMENTS

| 2,435,403 | A | | 2/1948 | Morris |
| 3,437,701 | A | | 4/1969 | Capaldi |
| 4,286,109 | A | * | 8/1981 | Norton ..................... C10L 1/04 149/109.4 |
| 5,516,953 | A | * | 5/1996 | Feldman ................... C07C 6/04 585/365 |
| 7,846,222 | B2 | | 12/2010 | Renninger et al. |
| 8,703,454 | B2 | | 4/2014 | Schalk et al. |
| 2008/0092829 | A1 | | 4/2008 | Renninger et al. |
| 2009/0020089 | A1 | | 1/2009 | Ryder et al. |
| 2009/0020090 | A1 | | 1/2009 | Ryder et al. |

(Continued)

OTHER PUBLICATIONS

"Solvent-Free Conversion of Linalool to Methylcyclopentadiene Dimers: A Route to Renewable High-Density Fuels"; ChemSusChem, 4 (2011), pp. 465-469.*

(Continued)

*Primary Examiner* — Philip Louie
*Assistant Examiner* — Aaron Pierpont
(74) *Attorney, Agent, or Firm* — Charlene A. Haley

(57) ABSTRACT

A method to generate cyclic hydrocarbons from farnesene to increase both the density and net heat of combustion of the product fuels.

14 Claims, 12 Drawing Sheets

(56) References Cited

U.S. PATENT DOCUMENTS

| | | |
|---|---|---|
| 2009/0272119 A1 | 11/2009 | Ryder |
| 2009/0272352 A1 | 11/2009 | Ryder |
| 2011/0028773 A1 | 2/2011 | Subramaniam |
| 2013/0298861 A1 | 11/2013 | Lee et al. |

OTHER PUBLICATIONS

U.S. Appl. No. 13/676,541, Benjamin Harvey, related case.
U.S. Appl. No. 13/604,115, Benjamin Harvey, related case.
Meylemans, et al Solvent-free conversion of linalool to methylcyclopentadiene dimers. ChemSusChem, 4(2011), pp. 465-469.

* cited by examiner

US 9,963,651 B1

HIGH DENSITY CYCLIC FUELS DERIVED FROM LINEAR SESQUITERPENES

CROSS-REFERENCE TO RELATED APPLICATIONS

This is a non-provisional patent application, claiming the benefit of, provisional patent application Ser. No. 61/840322 filed on Jun. 27, 2013, and is a continuation-in-part of patent application, claiming the benefit of, Ser. No. 13/604,115 filed on Sep. 5, 2012 which is a non-provisional application, claiming benefit of, provisional application Ser. No. 61/531970 filed on Sep. 7, 2011, and is a continuation-in-part of, claiming the benefit of, Ser. No. 13/676541 filed on Nov. 14, 2012, which is a non-provisional application, claiming the benefit of, 61/562681 filed on Nov. 22, 2011, whereby the entire disclosure of which is incorporated by reference.

STATEMENT REGARDING FEDERALLY SPONSORED RESEARCH OR DEVELOPMENT

The invention described herein may be manufactured and used by or for the government of the United States of America tor governmental purposes without the payment of any royalties thereon or therefor.

Field of the Invention

The invention generally relates to a method to generate cyclic organic compounds including high-density cyclic fuels from bio-derived isoprenoid feedstocks.

Figure 1:
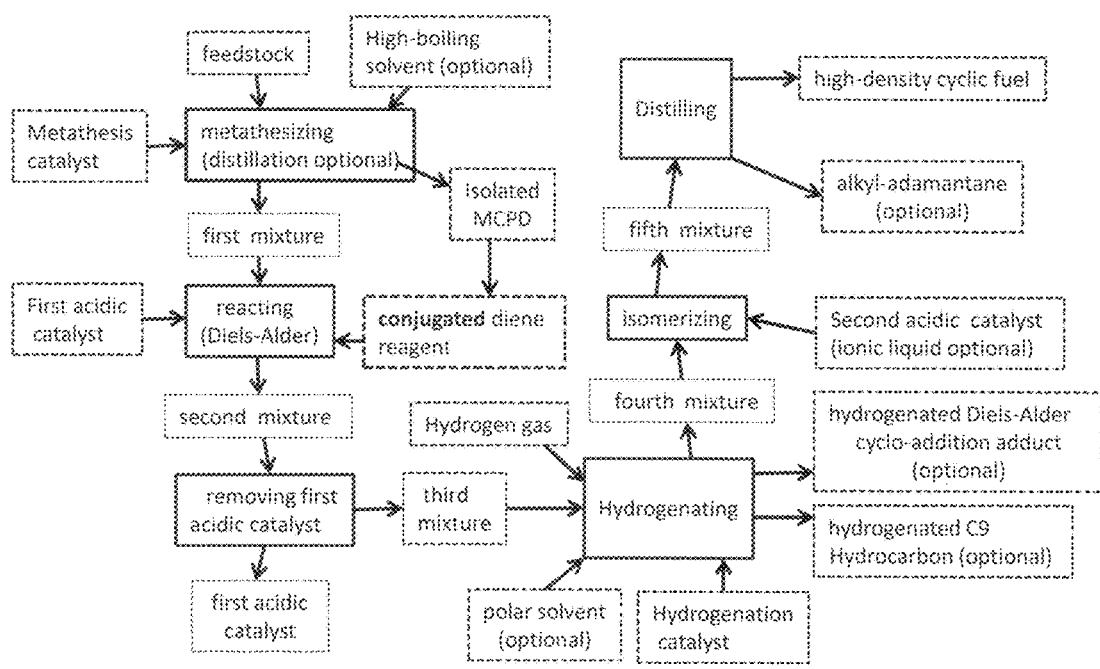
FIG. 1 is a general process flow diagram tor making high-density cyclic fuels according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

The invention generally relates to a method to generate cyclic hydrocarbons from linear sesquiterpenes to increase both the density and net heat of combustion of the linear-sesquiterpene product fuels, and more generally relates to a method to generate cyclic organic compounds from bio-derived isoprenoid feedstocks.

High density fuels have the potential to significantly increase the range, loiter time. and payload of a variety of Navy platforms. Derivation of these fuels from sustainable sources decreases Navy dependence on petroleum and has the added benefit of reducing carbon emissions. Embodiments of the invention describe a novel method of cyclizing sesquiterpenes and related hydrocarbons through the use of an efficient ring closing metathesis reaction, and hydrogenating the resulting products. This method greatly increases the density and volumetric net heat of combustion of the product fuels and can be tailored to production of multiple fuel products.

Linear sesquiterpenes are a subcategory of isoprenoids. Isoprenoid feedstocks are embodiment of the invention. Farnesene is a linear sesquiterpene and is used as an example feedstock. Farnesene may be isolated and produced from renewable sources. Farnesene may be derived from monosaccharide, disaccharide, polysaccharide, glucose, galactose, mannose, fructose, ribose, sucrose, lactose, maltose, trehalose, cellobiose, starch, glycogen, cellulose, chitin, and combinations of two or more thereof. Farnesene may be isolated from a variety of plants by various processes including extraction with solvents and steam distillation. Alternatively, farnesene may be generated from feedstocks including sugar, biomass, and $CO_2$ by a fermentation process or by direct biosynthesis.

Although hydrogenated farnesene has been shown to be a good candidate for renewable jet and diesel fuels, it suffers from relatively low density and low volumetric net heat of combustion that limits the amount that can be blended in commercial or military jet and diesel fuel. To overcome this limitation, embodiments of the invention describe a method to generate cyclic hydrocarbons from farnesene (and other isoprenoid feedstocks) to increase both the density and net heat of combustion of the product fuels. The high density hydrocarbons produced by this method have applications for missile, unmanned aerial vehicle, jet, and diesel propulsion.

Isomers of farnesene are produced by a variety of plants and are present in essential oils including that of gardenia. Farnesene has two structural isomeric forms, namely the A isomer:

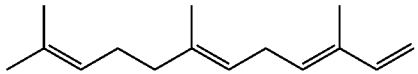

and the B isomer:

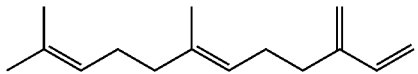

Figure 12:
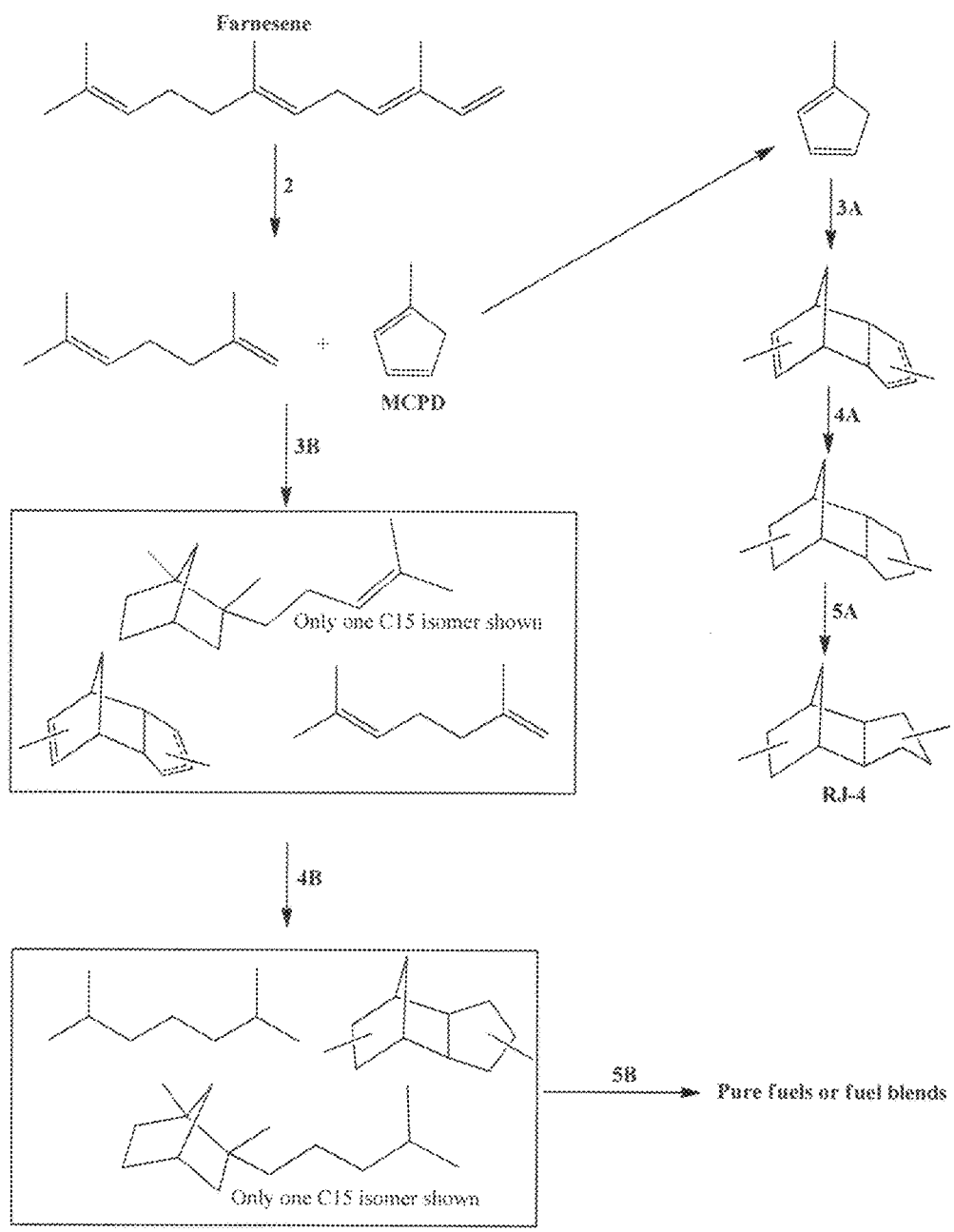
FIG. 12 is a flow chart showing methods to generate cyclic organic compounds including high-density cyclic fuels from bio-derived isoprenoid feedstocks, according to embodiments of the invention.

Using farnesene isomer A as an example, FIG. 12 shows reaction chemistry to make cyclic fuels, which is an embodiment of the invention. FIG. 12. An example of chemical reactions embodied in the invention used to make cyclic fuels: metathesis reactions (2), Diels-Alder reactions (3A and 3B), hydrogenation reactions (4A and 4B), and isomerization reactions (5A and 5B). FIG. 12 is a flow chart showing reaction chemistry to make cyclic fuels, according to embodiments of the invention.

In FIG. 12, farnesene is allowed to react with a metathesis catalyst to produce a first mixture having methylcyclopentadiene (MCPD) and C9 branched-chain hydrocarbon. A small amount of higher molar muss compounds, including C28 may also be formed. The MCPD may be isolated by distillation. The MCPD may then be subjected to conditions in which two molecules of MCPD undergo a Diels-Alder reaction to generate MCPD dimer. The MCPD dimer may be isolated, hydrogenated, and isomerized to form RJ-4 fuel. In another embodiment of the invention, a first mixture of MCPD and C9 branched-chain hydrocarbon undergoes Diels-Alder reactions that generate a second mixture including MCPD dimer, a cyclic C15 hydrocarbon, and unreacted C9 hydrocarbon. Reaction products in this second mixture may be hydrogenated to form a hydrogenated mixture including C9, C12, and C15 saturated hydrocarbons that may be used as a fuel. Furthermore, this hydrogenated mixture may be fractionally distilled to isolate pure products, or specific mixtures of saturated hydrocarbons, which individually or blended together may be used as fuels.

As embodiments of the invention farnesene feedstock is allowed to react with a metathesis catalyst. The catalyst may be homogenous or heterogeneous. The metathesis catalyst includes one or more active transition metals including, but not limited to, ruthenium, molybdenum, tungsten, and rhenium. Heterogeneous metathesis catalysts that may be used are one or more of these same transition-metals supported on a solid supporting material. Examples of such solid supporting materials are zeolites, silica, alumina, aluminosilicates, zirconia, titania, other metal oxides, activated carbon, other carbon supports, cross-linked polystyrene, macroreticular resins, and other polymer-based supports.

In the temperature range of about 0° to about 150° C. under inert-gas atmosphere farnesene undergoes a ring-closing metathesis reaction that generates methylcyclopentadiene (MCPD) and a branched chain C9 hydrocarbon.

FIG. 1 is a general process flow diagram that is an embodiment of the invention showing reagents, catalysts, reactions and isolations that may be involved in producing high-density cyclic fuels. In embodiments, MCPD may be effectively separated from the metathesizing reaction mixture by running the reaction at a temperature above the boiling point of MCPD, distilling the reaction mixture, and removing MCPD from a reflux column with a condenser (herein called isolation by distillation or distillative removal). MCPD is removed to increase the yield of the metatheszing reaction. At the completion of the metathesizing reaction, MCPD (and/or other conjugated dienes), is added to the Diels-Alder reacting reaction chamber (the reacting (Diels-Alder) box in FIG. 1). Examples of other dienes that may be used in the Diets-Aider reaction, are cyclopentadiene, terpinene, other cyclic conjugated dienes, butadiene, and isoprene (which are other embodiments of the invention).

Other embodiments of the invention include a metathesis reaction that may be carried out in a high-boiling solvent, including under a partial vacuum, that allows the MCPD to be removed as it is formed using a reflux column, a condenser, or a cold trap. Examples of high-boiling solvents that are embodiments of the invention are decalin, xylene, and other non-protic solvents that have a boiling temperature at standard conditions ranging from about 100° C. to about 200° C.

Methylcyclopentadiene and other conjugated dienes undergo exothermic DielsAlder cycloadditions. This reaction will occur uncatalyzed at room temperature. [Caution: when MCDP is stored in a sealed container, the exothermic heat released during dimerization may cause a violent rupture of the container.] As embodied in the invention, the rate of Diels-Alder cycloaddition can be increased by increasing the temperature, adding an acidic catalyst, increasing the pressure, or combining any of these methods. The acidic catalyst may be homogeneous or heterogeneous. The acidic catalyst may be a Lewis acid. A heterogeneous Lewis-acid catalyst, which is an embodiment of the invention, may be supported on at least one solid material, including zeolites, aluminosilicate, alumina, zirconia, titania, silica, clay, other metal oxides, cross-linked sulfonated polystyrene, other macroreticular resin, other polymers, crosslinked ionic liquids, crosslinked poly(ionic liquid), and crosslinked ionic liquid gels.

The resulting MCPD dimer and other Diels-Alder adducts are hydrogenated with hydrogen gas using a homogenous or heterogeneous catalyst to form hydrogenated dimers. The hydrogenation catalyst has an active metal, or alloy of metals, including but not limited to Ni, Ru, Pd, Pt, or Cu. Hydrogen pressure may range from about 1 atmosphere to about 100 atmospheres (atm), where 1 atm=760 torr (a standard definition), and the temperature may range from about 0 degrees to about 250 degrees C. As an embodiment of the invention, the hydrogenation reaction may be carried out in the presence of a polar organic solvent to improve the yield of hydrogenated products. Examples of useful polar solvents that may be added are ethyl acetate, other organic esters, acetic acid, other organic acids, methanol, ethanol, other alcohols, THF, dioxane, and other ethers.

The hydrogenated dimers are then isomerized with a strong second acidic catalyst, including a Lewis acid (e.g. $AlCl_3$), $AlCl_3$-derived ionic liquid, or other Lewis acid to generate the missile fuel RJ-4. The Lewis acid may be homogeneous or heterogeneous. The homogeneous Lewis acid may be selected from at least one of the group consisting of $AlCl_3$, $FeCl_3$, $TiCl_4$, $ZnCl_2$, $SbF_5$, $BF_3$, and other homogeneous Lewis-acid compounds based on metals including Ti, V, Cr, Mn, Fe, Co, Ni, Cu, Zn, B, Al, Sn, and Sb. The isomerizing may also be carried out in the presence of an ionic liquid. Examples of such ionic liquids are pyridinium ionic liquid, imidazolium ionic liquid, acidic ionic liquid, acidic chloroaluminate ionic liquid, clay-supported chloroaluminate ionic liquid, [1-butyl-3-methylimidazolium][bis(trifluoromethylsulfonyl imide)], [1-butyl-3-methylimidazolium][tricyanomethanide], [tri(butyl)(tridecyl)phosphonium][bis(trifluoromethylsulfonyl imide)], triethylammonium chloroaluminate, [1-butyl-3-methylpyridinium] chloroaluminate, and [1-butyl-3-methylimidazolium] chloroaluminate. The heterogeneous Lewis acid may be selected from the group consisting of $AlCl_3$, $FeCl_3$, $TiCl_4$, $ZnCl_2$, $SbF_5$, $BF_3$, and other Lewis-acid compounds based on metals including Ti, V, Cr, Mn, Fe, Co, Ni, Cu, Zn, B, Al, Sn, and Sb. Furthermore, the heterogeneous Lewis acid may be supported on at least one solid material selected from the group consisting of zeolites, aluminosilicates, alumina, zirconia, titania, silica, clays, other metal oxides, cross-linked sulfonated polystyrene, other macroreticular resin, other polymers, crosslinked ionic liquid, crosslinked poly(ionic liquid), and crosslinked ionic liquid gels.

The hydrogenated mixture may be used directly as a fuel, or the C9 hydrocarbon may be removed by fractional distillation to yield a high density jet/diesel fuel having hydrogenated methylcyclopentadiene dimers and cyclic C15 hydrocarbons. In other embodiments of the invention, olefins having the base formula A: R=CH—CH=C($CH_3$)—CH=$CH_2$, wherein R is selected from the group consisting of alkyl, cycloalkyl, functionalized alkyl, alkenyl, functionalized alkenyl, alkynyl, functionalized alkynyl, aromatic group, functionalized aromatic group and any combination thereof, may be converted to high-density cyclic fuels.

An example of an isoprenoid feedstock that is an embodiment of the invention is linalool. Embodiments of the invention generally relate to a highly efficient method for the conversion of a natural product into the high density fuel RJ-4 with concomitant evolution of isobutylene for conversion to fuels and polymers. More specifically, embodiments of the invention relate to efficient methods for the conversion of the renewable, linear terpene alcohol, linalool into a drop-in, high density fuel suitable for ramjet or missile propulsion. In line with Navy goals, these embodiments have the potential to decrease net carbon emissions of various platforms while maintaining optimum performance.

Fuels suitable for missile propulsion have multi-cyclic structures that impart high density while maintaining suitable low temperature viscosity. These fuels are particularly difficult to produce from renewable sources given their stringent requirements. Embodiments of this invention describe a highly efficient method for the conversion of the naturally occurring terpene alcohol, linalool, into the high density fuel RJ-4 which is composed of hydrogenated methylcyclopentadiene dimers. Recent work has shown that terpene alcohols and related molecules can be produced from cellulose with bioengineered organisms. In conjunction with the embodiments of this invention, this will allow for the sustainable and renewable production of a high density fuel from waste biomass. In addition to the production of RJ-4, embodiments of this invention generate isobutylene as a side-product which can be isolated and convened to gasoline, jet fuel, or polymers/elastomers.

The ring closing metathesis (RCM) of linalool to produce 1-methylcyclopent-2-enol and isobutylene using Ru-metathesis catalysts has been demonstrated in the literature. However, previous methods have utilized elevated temperatures, dilute solutions in chloroform, and in general, high catalyst loadings. This is in contrast to embodiments of this invention method which are perforated without solvent and at loadings as low as 0.01 mol %.

Embodiments of the invention relate to a method for manufacturing high density fuels including, reacting at least one terpene alcohol with at least one Ru-metathesis catalysis with a solvent or under solvent-tree conditions to produce 1-methylcyclopent-2-enol, dehydrating the 1-methylcyclopent-2-enol with at least one heterogeneous dehydration catalyst to produce methylcyclopentadienes, thermal dimerizing of the methylcyclopentadienes to produce methylcyclopentadiene dimers, hydrogenating the methylcyclopentadiene dimers with at least one hydrogenation catalyst to produce hydrogenated methylcyclopentadiene dimers, and isomerizing the hydrogenated methylcyclopentadiene dimers with at least one Lewis acid catalyst to produce high density fuels. Other embodiments of the invention relate to a method for producing fuels and/or byproducts including, reacting at least one terpene alcohol with at least one Ru-metathesis catalysis under solvent-free conditions to produce isobutylene, and oligomerizing the isobutylene with at least one oligomerization catalyst to produce at least one of the fuels and/or byproducts selected from the group consisting of gasoline, jet fuel, and polymers/elastomers.

Another aspect of the invention is the high density fuels, gasoline products, jet fuels, polymer-elastomer products, and fuel blends produced either by one or a combination of the methods therein. Another aspect of the invention relates to a method for manufacturing high density fuels including, reacting at least one terpene with at least one Ru-metathesis catalysts with a solvent or under solvent-free conditions to produce 3-methylenecyclopent-1-ene, isomerizing the 3-methylenecyclopent-1-ene with at least one isomerization catalyst to produce methylcyclopentadienes, thermal dimerizing of the methylcyclopentadienes to produce methylcyclopentadiene dimers, hydrogenating the methylcyclopentadiene dimers with at least one hydrogenation catalyst to produce hydrogenated methylcyclopentadiene dimers, and isomerizing the hydrogenated methylcyclopentadiene dimers with at least one Lewis acid catalyst to produce high density fuels.

Embodiments of the invention include at least one terpene alcohol is linalool. Other embodiments include at least one Ru-metathesis catalysts is selected from the group consisting of first generation Grubbs catalyst, second generation Grubbs, Grubbs-Hoveyda catalyst, catalysts with electron withdrawing alkoxides and labile pyridine ligands, and any metathesis catalyst tolerant of alcohols, including heterogeneous metal oxides and polymer supported catalysts. In embodiments, at least one heterogeneous dehydration catalyst is selected from the group consisting of $AlPO_4$, $Al_2O_3$, silica, $MgSO_4$, zeolites, and molecular sieves. In other embodiments, the thermal dimerizing method includes increasing the temperature to accelerate the dimerization of the methylcyclopentadienes to produce methylcyclopentadienes dimers. In other embodiments, the thermal dimerizing method includes utilizing room temperature to dimerize the methylcyclopentadienes to produce methylcyclopentadiene dimers.

In embodiments, a Lewis acid catalyst is employed to increase the rate of dimerization of methylcyclopentadienes. In embodiments, at least one hydrogenation catalyst includes at least one of Ni, Pd, Pt, and Cu, either supported or unsupported. In embodiments, at least one Lewis acid catalyst for isomerization of tetrahydrodimethylcyclopentadienes is selected from the group consisting of $AlCl_3$, ionic liquids and salts including $AlCl_4^-$ as the anion, and other homogenous or heterogeneous Lewis acids. In embodiments, the high density fuels is tetrahydrodimethylcyclopentadiene (RJ-4). In other embodiments, at least one oligomerization catalyst is selected from the group consisting of supported polyphosphoric acid, zeolites, metal oxides, cation exchange resins, Lewis acids, and acid clays. In embodiments, the at least one terpene is myrcene (see Scheme 7).

Aspects of the invention relate to a highly efficient method for the conversion of a natural product into the high density fuel RJ-4 with concomitant evolution of isobutylene for conversion to fuels and polymers as shown in Schemes 2 and 3.

Scheme 1.

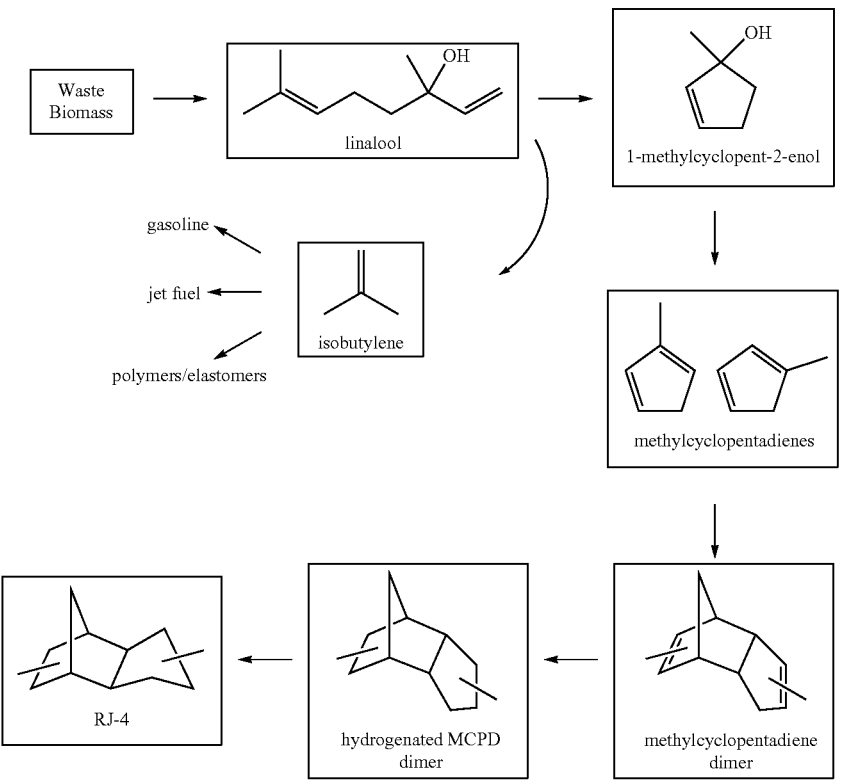

Scheme 2.

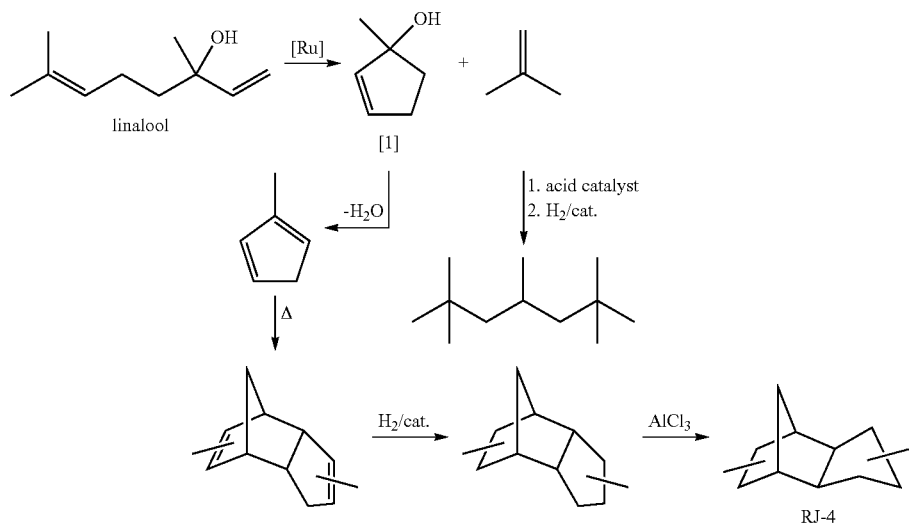

The development of techniques for the efficient synthesis of custom fuels and chemicals from sustainable natural feedstocks is of fundamental importance to society as the direct and indirect costs of petroleum use continue to increase. (A. J. Ragauskas. C. K. Williams, B. H. Davison, G. Britovsek, J. Cairney. C. A. Eckert, W. J. Frederick, J. P. Hallet, D. J. Leak, C. L. Liotta, J. R. Mielenz, R. Murphy, R. Templer, T. Tschaplinski, *Science* 2006, 311, 484-489, b) G. W. Huber, S. Iborra, A. Corma, *Chem. Rev.* 2006, 106, 4044-4098. c) J. Hill, *Sust. Agric.* 2009, 125-139). For general transportation fuels, complex mixtures or molecules that have somewhat lower utility than petroleum based analogs may be sufficient, however for specific applications such as jet and missile propulsion, a more selective model that produces molecules with defined and specialized properties is required. Well characterized, single-site catalysis is the basis of elegant synthetic strategies for the production of pure compounds. In particular, ruthenium-based olefin metathesis catalysts are known to catalyze a number of reactions including self-metathesis, cross-metathesis, ring closing metathesis (RCM) and ring opening metathesis polymerization (ROMP). (G. C. Vougioukalakis, R. H. Grubbs. *Chem. Rev.* 2010, 110, 1746-1787; A. H. Hoveyda, A. R. Zhugralin, *Nature* 2007, 450, 243-251. c) R. H. Grubbs, *Angew. Chemie Int'l. Ed.* 2006, 45, 3760-3765: R. H. Grubbs, *Tetrahedron* 2004, 60, 7117-7140; C. Samojlowicz, M. Bieniek, K. Greta, *Chem. Rev.* 2009, 109, 3708-3742). This family of catalysts is ubiquitous in the literature and has been used for everything from natural product synthesis to polymer chemistry. (D. E. White, I. C. Stewart, R. M. Grubbs, B. M. Stoltz. *J. Am. Chem. Soc.* 2008, 130, 810-811; M. Arisawa, A. Nishida, M. Nakagawa, *J. Organomet. Chem.* 2006, 691, 5109-5121; G. O. Wilson. M. M. Caruso, N. T. Reimer, S. R. White, N. R. Sottos, J. S. Moore, *Chem. Mater.* 2008, 20, 3288-3297: R. M. Thomas, R. H. Grubbs, *Macromolecules* 2010, 43, 3705-3709.) The transition of these catalysts to large scale industrial processes has in (lie past been hindered by their modest turnover numbers and high cost. (M. Ulman, R. H. Grubbs, *J. Org. Chem.* 1999, 64, 7202-7207. b) J. C. Conrad, J. L. Snelgrove, M. D. Eeelman, S. Hall, D. E. Fogg *J. Molec. Catal. A* 2006, 254, 105-110). To overcome these difficulties, catalytic systems need to be developed that can efficiently yield pure products while maintaining low catalyst loadings. In this specification, we detail a ruthenium catalyzed method for the synthesis of dimethyldicyclopentadiene from linalool, a linear terpene alcohol. Recent work in our lab has focused on the conversion of terpenes to high density fuel surrogates. (B. G. Harvey, M. E. Wright, R. L. Quintana *Energy Fuels* 2010, 24, 267-273). Although terpenes are naturally produced by pine trees and a variety of plants, a truly sustainable method may require the utilization of bioengineered microbes to produce specific molecules or families of molecules from waste cellulose. (M. C. Y. Chang, J. D. Keasling *Nature Chem. Bio.* 2006, 2, 674-681; F. M. Carrau, K. Medina. E. Boido, L. Farina, C. Gaggero, E. Dellacassa, G. Versini, P. A. Henschke, *FEMS Microbio. Lett.* 2005, 243, 107-115).

Within the terpene family, linalool is a particularly intriguing feedstock for fuels due to its molecular structure. Although the RCM of linalool must proceed through a sterically hindered transition state, the reaction is facilitated by coordination of the allylic alcohol. (T. R. Hoye, H. Zhao *Org. Lett.* 1999, 1, 1123-1125). This results in an efficient method for the synthesis of 1-methylcyclopent-2-enol (1) and isobutylene (Scheme 1). Both of these products are of significant interest as they can be converted to renewable fuel and polymer products. Isobutylene is a valuable side-product that can be selectively trimerized to produce jet fuel, dimerized, or alkylated with C4 raffinate to produce high octane gasoline, or polymerized to polyisobutylene. (R. Alcántara, E. Alcántara, L. Canoira, M. J. Franco, M. Herrera, A. Navarro, *React. Funct. Polym.* 2000, 45, 19-27; J. W. Yoon, S. H. Jhung, T-J. Kim, H-D. Lee, N. H. Jang, J-S. Chang, B*ull. Korean Chem. Soc.* 2007, 28, 2075-2078; D. M. Haskell, F. Floyd, U.S. Pat. No. 4,301,315, 1981; T. I. Evans, L. J. Karas, R. Rameswaran, U.S. Pat. No. 5,877,372, 1999; Y. Li, Y. Wu, L. Liang, Y. Li, G. Wu, Chin. *J. Polym. Sci.* 2010, 28, 55-62; V. Vasilenko, A. N. Frolov, S. V. Kostjuk, *Macromolecules* 2010, 43, 5503-5507; Q. Liu, Yi-X. Wu, Y). Meanwhile, 1 can be efficiently converted to methylcyclopentadiene dimer, which can be hydrogenated and isomerized to produce the high density missile fuel RJ-4. (G. W. Burdette, A. I. Schneider, U.S. Pat. No. 4,398,978, 1983; J. S. Chickos, A. E. Wentz, D. Hillesheim-Cox, *Ind. Eng. Chem. Res.* 2003, 42, 2874-2877 (Scheme 1)).

NMR scale conversions of linalool to 1 under dilute conditions and at elevated temperatures have been reported in the literature. Catalysts used for this reaction (Scheme 3) have included the first generation Grubbs catalyst (2), both a second generation Grubb's (5) and Grubbs-Hoveyda catalyst (4), as well as catalysts with electron withdrawing alkoxides and labile pyridine ligands (6,7). (D. C. Braddock, A. Matsuno, *Tet. Lett.* 2002, 43, 3305-3308; J. C. Conrad, H. H. Parnas, J. L. Snelgrove, D. E. Fogg, *J. Am. Chem. Soc.* 2005, 127, 11882-11883). More recently the RCM of linalool and several other substrates has been studied with ruthenium catalysts functionalized with N-napthyl substituted heterocyclic carbene ligands. (L. Vieille-Petit, H. Clavier, A. Linden, S. Blumentritt, S. P. Nolan, R. Dorta, *Organometallics* 2010, 29, 775-788) Among these examples, the alkoxide functionalized catalysts are particularly notable as they were able to achieve 100% conversion in 15 min at 0.5 mol % loading and in some cases, full conversion in one h at 0.05 mol % loading in refluxing chloroform. This is in contrast to the other catalyst studies that utilized relatively high catalyst loadings (1-5%) to achieve high conversion efficiencies (Table 1). Although these preliminary studies were intriguing, the work in our laboratory focused on maximizing the turnover number (TON) for the RCM of linalool while reducing the use of extraneous solvents and the energy footprint of the process (a key requirement for the synthesis of renewable fuels). To help accomplish this, all of the reactions were run neat, a condition that has been shown to be effective in promoting high TONs for certain substrates. (M. B. Dinger, J. C. Mal, *Adv. Synth. Catal.* 2002, 344, 671-677).

Scheme 3. Structure of selected ruthenium metathesis catalysts that have been studied for the RCM of linalool.

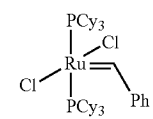

2

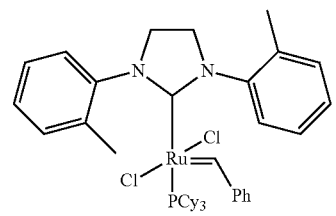

3

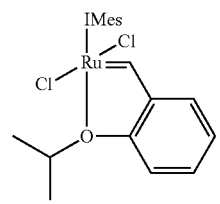

4

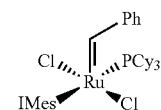

5

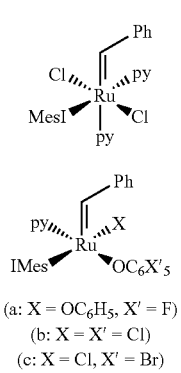

(a: X = OC₆H₅, X' = F)
(b: X = X' = Cl)
(c: X = Cl, X' = Br)

TABLE 1

Reaction conditions and yield of 1 for a series of ruthenium metathesis catalysts

| Catalyst | Loading (mol %) | Temp | Time | Solvent | Yield |
|---|---|---|---|---|---|
| 2 | 0.1 | ambient | 16 h | neat | 0 |
| 2 | 0.1 | 45 | 1 h | neat | 55 |
| 3 | 0.1 | 60 | 30 min | neat | 36 |
| 3 | 0.01 | ambient | 16 h | neat | 0 |
| 3 | 0.01 | 60 | 30 min | neat | 18 |
| 4 | 0.1 | ambient | 45 min | neat | 100 |
| 4 | 0.01 | ambient | 1 h | neat | 44 |
| 5, 6, 7a, 7b, 7c | 0.5 | 60 | 15 min | CDCl₃ | 100 |
| 5, 6, 7a, 7b, 7c | 0.05 | 60 | 1 h | CDCl₃ | 24, 29, 100, 17, 34 |

As the first slep in the development of a large scale synthesis of the high density fuel RJ-4 from a renewable source, the solvent-free, preparative scale RCM of linalool with three commercial catalysts was studied. The first generation Grubbs catalyst 2, a second generation Grubbs catalyst with a sterically open N-heterocyclic carbene ligand 3, and a second generation Grubbs-Hoveyda catalyst 4 were screened for activity. For catalyst 2, attempts to decrease the loading to 0.1 mol % resulted in incomplete conversion to the alcohol. No reaction was observed at room temperature, while reaction at 45° C. resulted in 55% conversion after one hour, increasing the reaction time did not lead to further reaction. Catalyst 3 which was chosen based on its well established activity in the RCM of sterically hindered substrates produced no discernible product after 16 h at ambient temperature with either 0.1 or 0.01 mol % loading, however at 60° C., yields of 36 and 18% were obtained, respectively. Unfortunately, catalyst 3 deactivated within 30 minutes at this temperature, a result that was not surprising given the reported modest thermal stability of this catalyst. (I. C. Stewart. T. Ung. A. A. Pletnev, J. M. Berlin. R. H. Grubbs, Y. Schrodi, *Org. Lett.* 2007, 9, 1589-1592).

Figure 2:
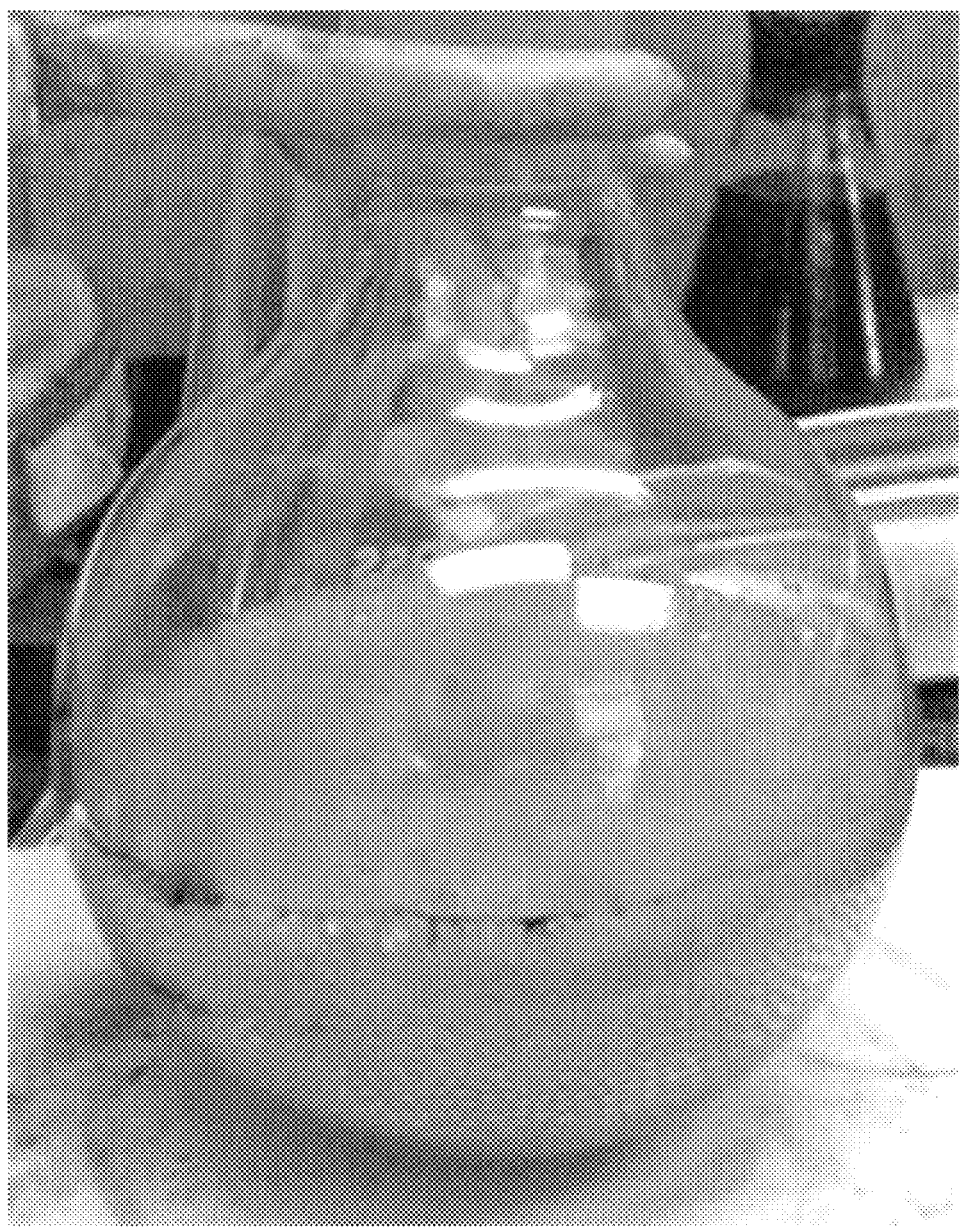
FIG. 2 is a photograph of the room temperature, solvent free reaction of linalool with catalyst at five minutes after addition, according to embodiments of the invention.

FIG. 2 is a photograph of the room temperature, solvent-free reaction of linalool with catalyst 4 at five minutes after addition. Vigorous bubbling is due to production of isobutylene. To improve the conversion efficiency, the more stable catalyst 4 was evaluated at a loading of 0.1 mol %. At room temperature the reaction proceeded rapidly (FIG. 2) with copious production of isobutylene. By this method linalool was converted quantitatively to 1 in 45 min at ambient temperature. At 0.01 mol % loading, a 44% conversion to the alcohol was achieved in one h, representing a remarkable TON of 4400. Reaction for longer periods of time resulted in no improvement in yield. Based on the catalyst screening, 4 was utilized in preparative scale (30 g) syntheses of 1. Isobutylene was either collected with a dry ice condenser or allowed to escape through a bubbler. At the conclusion of the reaction, the product was isolated by vacuum distillation at room temperature; yields of >95% were routinely achieved.

In an attempt to improve the conversion efficiencies of catalysts 2 and 4, the effect of increasing the temperature was studied. Interestingly, when either 2 or 4 were used as the catalyst, a reaction temperature of 60° C. resulted in partial conversion of 1 to methylcyclopentadiene (MCPD). GC/MS analysis of the reaction mixture showed that linalool had been converted to a complex mixture of 1, cyclopentenol ethers, MCPD, and methylcyclopentadiene dimers (Scheme 4). In effect it appeared that 2 and 4 were acting as dehydration catalysts. Interestingly, for 4, this same effect was not observed when sufficient linalool was present in solution. As a control, a 0.01 mol % solution of catalyst 4 in linalool was prepared. After the reaction had proceeded to 44% conversion, the mixture was heated to 60° C. for 16 h. No dehydration of the product was observed. It is also important to note that catalyst decomposed through air exposure was not active for the dehydration of the alcohol. Rapid stirring of the flask in open air or alternatively active bubbling of air into the reaction flask resulted in a color change from green to brown-black. This oxidized mixture was much less prone to dehydration reactions.

Although the dehydration reaction appeared to be mediated by the ruthenium catalyst, another possibility is that the catalyst reacted with linalool, 1, or water to exchange alkoxide or hydroxide ligands with the chloride ligands. This process would release catalytic amounts of HCl which could then lead to dehydration of the alcohol. To investigate the extent to which a Lewis acid would dehydrate 1, the alcohol was allowed to react with the Lewis acids PdCl₂(PhCN)₂ and Ru(COD)Cl₂ at room temperature in CDCl₃. As a control, Pd(0) (5% Pd/C) was also evaluated as a catalyst for the dehydration of 1. Interestingly, all of the catalysts converted 1 to similar mixtures of dehydrated products comparable to those observed with the metathesis catalysts. Further observation revealed that although neat samples of 1 were stable indefinitely in closed flasks at room temperature. NMR samples in CDCl₃ slowly converted to dehydrated mixtures, albeit at a much slower rate than for the Lewis acid catalyzed reactions. Given the known decomposition of chloroform to produce HCl and phosgene, it seems likely that even this small amount of acid was sufficient to promote the dehydration of the alcohol.

Scheme 4. Mechanism for the acid catalyzed dehydration of 2-methyl-1-cyclopentenol.

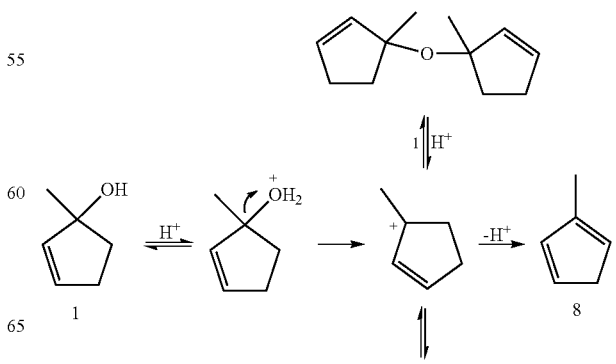

-continued

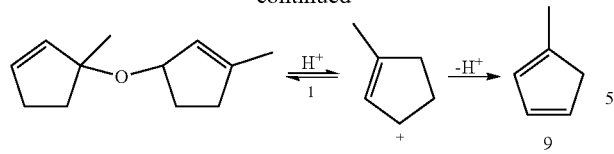

Although the Ru-catalysts showed some modest activity for the partial dehydration of 1, more efficient and selective methods were sought to convert 1 to MCPD. Given the rapid room temperature conversion of MCPD to dimer, particularly in the presence of acid catalysts, two distinct routes to the dimer were conceived. In the first route, a solid acid catalyst would be employed and the dehydration and dimerization would occur in the same flask. In the second route, a dehydration catalyst of much lower acidity would be employed and the reaction carried out under reduced pressure, allowing the volatile MCPD to be easily separated from the reaction mixture. For the first route, heterogeneous solid acid catalysts were employed to allow tor easy isolation of the product. Montmorillonite K10 (MMT-K10), an acid clay, and Nafion SAC-13, a silica supported perfluorinated cation exchange resin were screened for activity. Although both catalysis resulted in high conversions (95% conversion in one hour at ambient temperature), both yielded complex mixtures consisting of ether, dimer, significant amounts of trimer, and other heavier oligomers (Table 2). To try and trap MCPD prior to oligomerization, the reaction was conducted with Nafion SAC-13 at 40° C. under reduced pressure (40 torr). Although the isolated MCPD was >90% pure, the yield was low and the reaction mixture rapidly oligomerized to a thick orange oil composed of heavy oligomers. From this result it was clear that in the case of strong heterogeneous acid catalysis, oligomerization occurred more rapidly than MCPD could be removed from the reaction flask.

To further investigate optimal dehydration conditions, a series of weak Bronsted and Lewis acid catalysis were screened to determine their activity in the selective dehydration of 1 (Table 2). Benzoic acid and dilute HCl were unselective and produced primarily ether along with dimer and trimer. Surprisingly, Pd(COD)Cl$_2$ reacted almost quantitatively and produced 66% dimer along with significant amounts of trimer and tetramer. In the search for a milder dehydrating agent, magnesium sulfate was employed as a catalyst and produced only ethers. In contrast to the other dehydration catalysis that produced primarily one ether isomer. MgSO$_4$ produced the two distinguishable ether isomers in nearly equal amounts. This difference in isomer distribution is attributed to the lack of suitable acid sites on the catalyst. In the absence of these sites the reaction is driven by the coordination of water to magnesium cations and is dependent on the auto-ionization of the alcohol. Based on these initial screening results, an aluminum phosphate catalyst was prepared and evaluated as a dehydration catalyst. (A. W. Wang, Final Report U.S. Department of Energy, Contract No. DE-FC22-94PC93052, 2002). Under a variety of conditions, this catalyst was selective for the production of only ethers, MCPD, and dimers; no heavier oligomers were formed. Despite the favorable product distribution, the conversion efficiency of this catalyst was limited by the production of water in the dehydration reaction. To overcome this hurdle, mixtures of AlPO$_4$ with suitable drying agent were employed. An AlPO$_4$/molecular sieve catalyst resulted in a low overall yield of MCPD with formation of an oligomeric mixture. In contrast, an AlPO$_4$/MgSO$_4$ catalyst permitted the direct conversion to MCPD. The optimized catalyst allowed for a 78% isolated yield of isomeric MCPD from 1.

TABLE 2

Catalysts for the dehydration of 1

| Catalyst | Temp | Time | Pressure | Products 1:ether:dimer:oligomer |
|---|---|---|---|---|
| MMT-K10 | 25 | 1 h | atm | 5:41:22:32 |
| Nafion SAC-13 | 25 | 1 h | atm | 6:35:23:36 |
| Pd(COD)Cl$_2$ | 25 | 16 h | atm | <1:14:66:23 |
| 2M HCl | 25 | 1 h | atm | 0:(86):13$^a$ |
| MgSO$_4$ | 25 | 16 h | atm | 16:84:0:0 |
| Benzoic Acid | 25 | 16 h | atm | 8:66:21:4 |
| AlPO$_4$/MgSO$_4$ | 60 | 5 h | 0.05 atm | 10:90:0:0$^b$ |

$^a$The number in parantheses is the mass % of ethers and dimers combined.
$^b$This distribution represents what was left in the reaction flask. A 78% isolated yield of MCPD isomers was obtained through this method.

Figure 3:
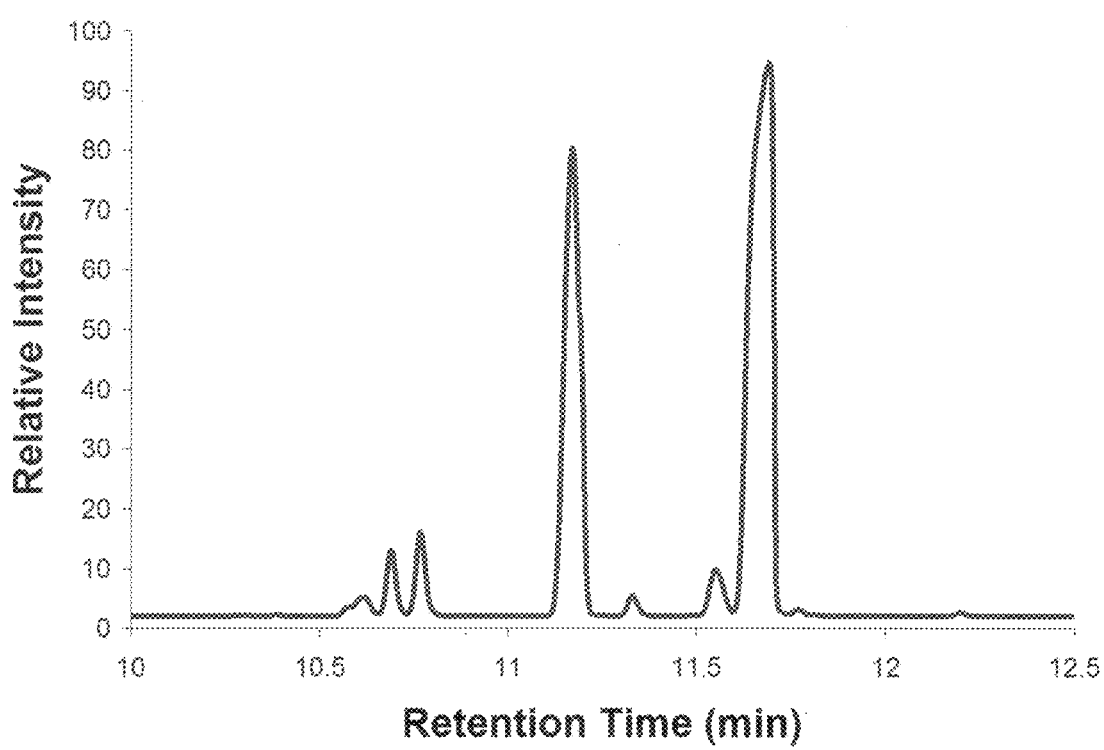
FIG. 3 is a graph illustrating a GC Chromatogram of MCPD dimers derived from dehydration of 1 with $AlPO_4$/$MgSO_4$ followed by ambient temperature dimerization, according to embodiments of the invention.

FIG. 3. GC Chromatogram of MCPD dimers derived from dehydration of 1 with AlPO$_4$/MgSO$_4$ followed by ambient temperature dimerization.

The dimer product distribution resulting from the room temperature Diels-Alder cycloaddition of MCPD is of significant interest and is in-part controlled by the starting composition of MCPD isomers. Dehydration of the alcohol with AlPO$_4$ at 60° C. yields 84% 2-methylcyclopentadiene (8) and 16% 1-methylcyclopentadiene (9), while 5-methylcyclopentadiene was not observed. The predominance of 8 results from the formation of a more stable tertiary carbocation compared to the secondary carbocation intermediate required for 9 (Scheme 4). In commercial methylcyclopentadiene dimer, seven peaks are observed in the gas chromatogram. (M. A. Diez, M. D. Guillen, C. G. Blanco, J. Bermejo, J. Chromatography 1990, 508, 363-374.) The distribution contains four major peaks representing various isomers resulting from the cycloaddition of 2-methyl and 1-methyl cyclopentadiene. The dimers are present almost exclusively as the endo isomers. In the current work, seven peaks are observed, however the distribution is significantly different than for the commercial product, with two peaks representing 88% of the dimers. The largest peak (56%) is observed for 3,9-dimethyl-endo-tricyclo[5.2.1.0$^{2,6}$]deca-3,8-diene (10), while the other main peak (55%) is observed for 4,9-dimethyl-endo-tricyclo[5.2.1.0$^{2,6}$]deca-3,8-diene (11) (Scheme 5). In comparison, the commercial product is 36% 10 and 29% 11. (W. Thommen, H. Pamingle, K. H. Schulte-Elte, Helv. Chim. Acta 1989, 72, 1346-1353). Coupling of two molecules of 8 yields 10, while coupling of 8 and 9 yields 11. The distribution of isomers is also dependent on both the relative dimerization rates of 8 and 9 as well as concomittant monomer isomerization. Previous studies have shown that 2-methylcyclopentadiene dimerizes faster than 1-methylcyclopentadiene ostensibly due to less steric crowding at the site of cycloaddition; this effect further influences the final distribution. (S. M. Csicsery J. Org. Chem. 1960, 25, 518-521).

Interestingly, dimer 12 which represents roughly 10% of commercial dimethyldicyclopentadiene is only 3% of the current mixture. This is likely the result of the known [3,3]-sigmatropic Woodward-Katz rearrangement to 11 being catalyzed by the dehydration conditions. (W. Thommen, H. Pamingle, K. H. Schulte-Elte, Helv. Chim. Acta 1989, 72, 1346-1353).

Scheme 5. Prominent endo-isomers produced form the thermal dimerization of MCPD isomers dervied from 2-methyl-1-cyclopentenol. The first number of a pair represents the % composition produced in this work, while the numbers in brackets refer to % composition of the commercial product.

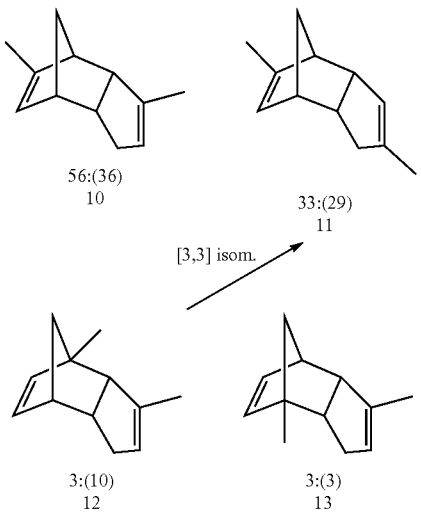

Scheme 6.

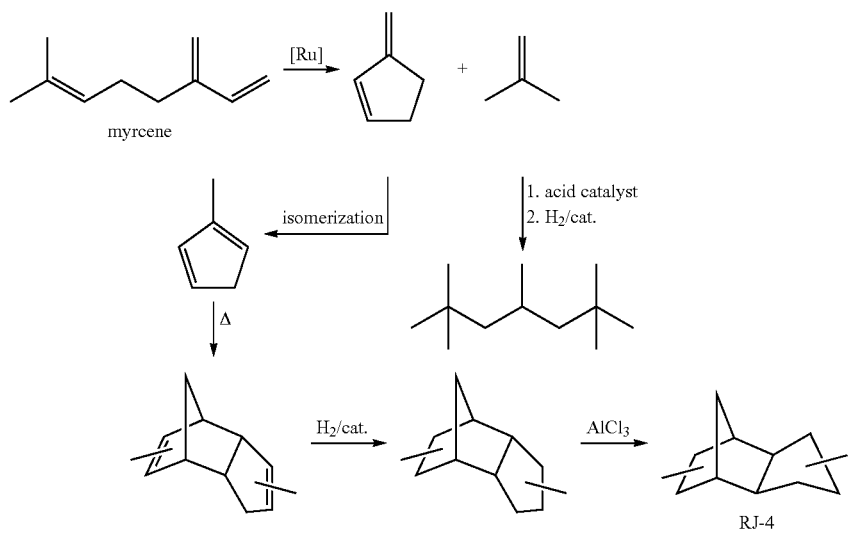

In order to convert the dimer mixture to RJ-4, it must first be hydrogenated. This was accomplished under mild conditions (40 psi, $PtO_2$ catalyst) and resulted in six distinguishable isomers. The four major peaks representing 91% of the product are the four sets of diasteriomers arising from the non-stereospecific hydrogenation of 10 and 11. After hydrogenation, these mixtures can be isomerized with strong Lewis acid catalysts to fuels rich in exo-isomers.

In summary, a highly efficient and selective synthesis for the conversion of linalool to specialized fuel products has been developed. The optimized approach offers a high catalyst turnover number, solvent free conditions, low external energy demands, and an exceptionally well defined product distribution. Further work to effectively reduce catalyst loadings and to establish how the distribution of dimers will affect the performance of high density fuel mixtures is ongoing.

Experimental Section

General: Grubbs 1st generation catalyst (2), Grubbs 2nd generation catalyst (3), and Grubbs-Hoveyda 2nd generation catalyst (4), were purchased from Aldrich, stored in a nitrogen filled glove box, and used as received. Linalool (97%, FG) was purchased from Aldrich and was distilled under reduced pressure and stored under nitrogen before use unless otherwise noted. $MgSO_4$ (Polarchem), 4 Å molecular sieves (Aldrich), MMT-K10 (Aldrich), Nafion SAC-13 (Aldrich), benzoic acid (Aldrich), $Al(NO3)_3$-$9H_2O$ (RG Aldrich), $H_3PO_4$ (85%, Fisher), and $NH_4OH$ (27%, Aldrich) were used as received. $^1H$ NMR measurements were performed using a Bruker AC 200 instrument. $^1H$ NMR chemical shifts are reported versus the deuterated solvent peak ($CDCl_3$, δ 7.25 ppm). Product mixtures were analyzed with an Agilent 6890-GC system with a Restek RTX-5MS 30-meter column. The QC inlet temperature was 250° C. and the column oven temperature was initially held at 40° C. for three minutes and then increased to 350° C. at 10° C./min. An Agilent mass selective detector (MSD) 5973 system was used to identify the sample's components.

EXAMPLE 1

General Preparative Scale Procedure for Synthesis of 1 from Linalool

Figure 4:
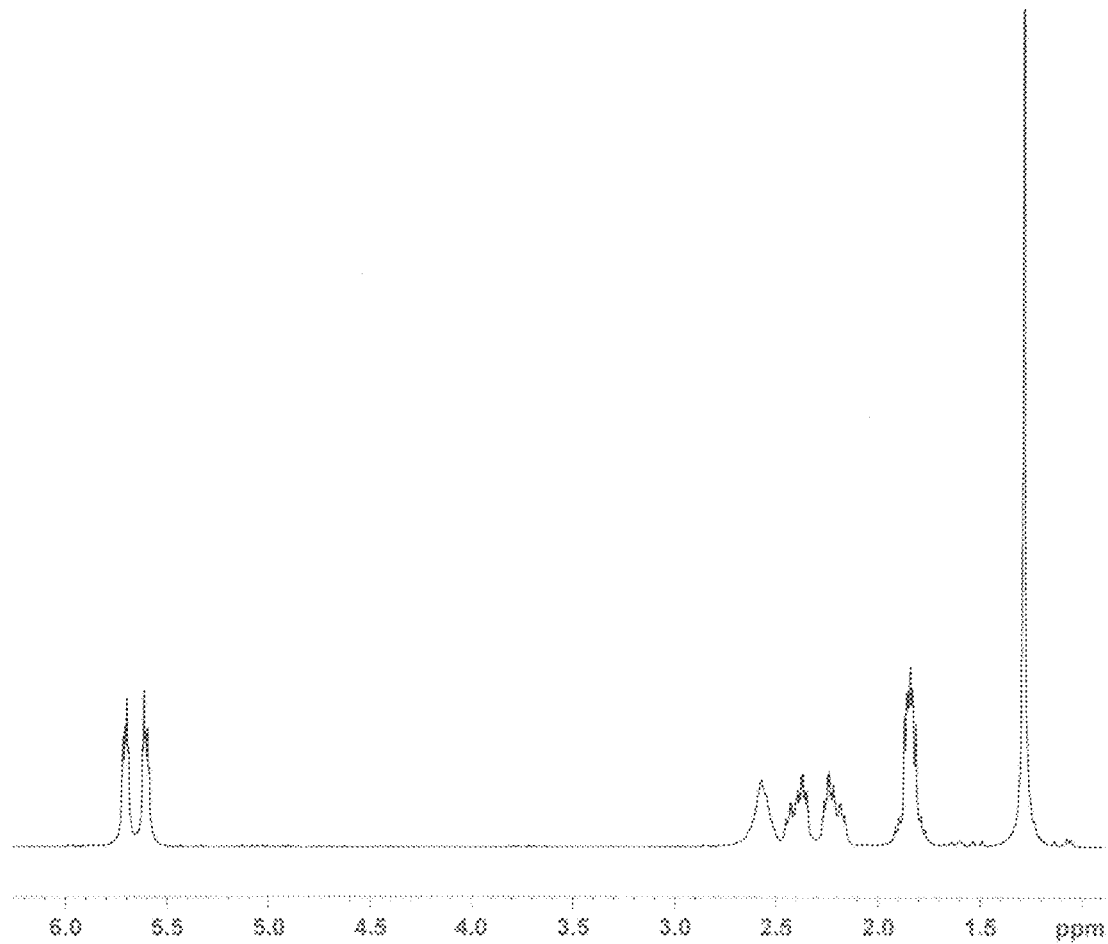
FIG. 4 is a graph that is a representative $^1H$ NMR of 1-methylcyclopent-2-enol produced by ROM of linalool, according to embodiments of the invention.

Reactions were run with 0.1 mol % of the Hoveyda-Grubbs 2nd generation catalyst. The catalyst was stored in the glove box and the required amount was removed in a round bottom flask charged with a stirbar and sealed with a septum. Linalool was transferred via syringe into the RBF containing the catalyst. At this point the flask was vented through an oil bubbler and within 30 seconds vigorous bubbling began while stirring at room temperature. The bubbling continued for 30-45 minutes and then ceased. Once bubbling had stopped air was bubbled into the reaction mixture for 15 minutes to ensure the catalyst was inactive. $^1$H NMR of the crude reaction mixture showed 100% conversion of starting linalool. The product was immediately vacuum transferred (1 torr) to a chilled flask (−78° C.). After transfer the product was sealed under nitrogen and stored at room temperature. The product was analyzed via NMR. $^1$H NMR (CDCl$_3$) δ: 1.29 (s, 3H), 1.84 (m, 2H), 2.23 (m, 1H), 2.37 (m, 1H), 2.57 (broad 8, 1H), 5.65 (m, 2H). FIG. 4. Representative $^1$H NMR of 1-methylcyclopent-2-enol produced by RCM of linalool.

EXAMPLE 2

RCM with Grubbs 1$^{st}$ Generation Catalyst (2)

Figure 5:
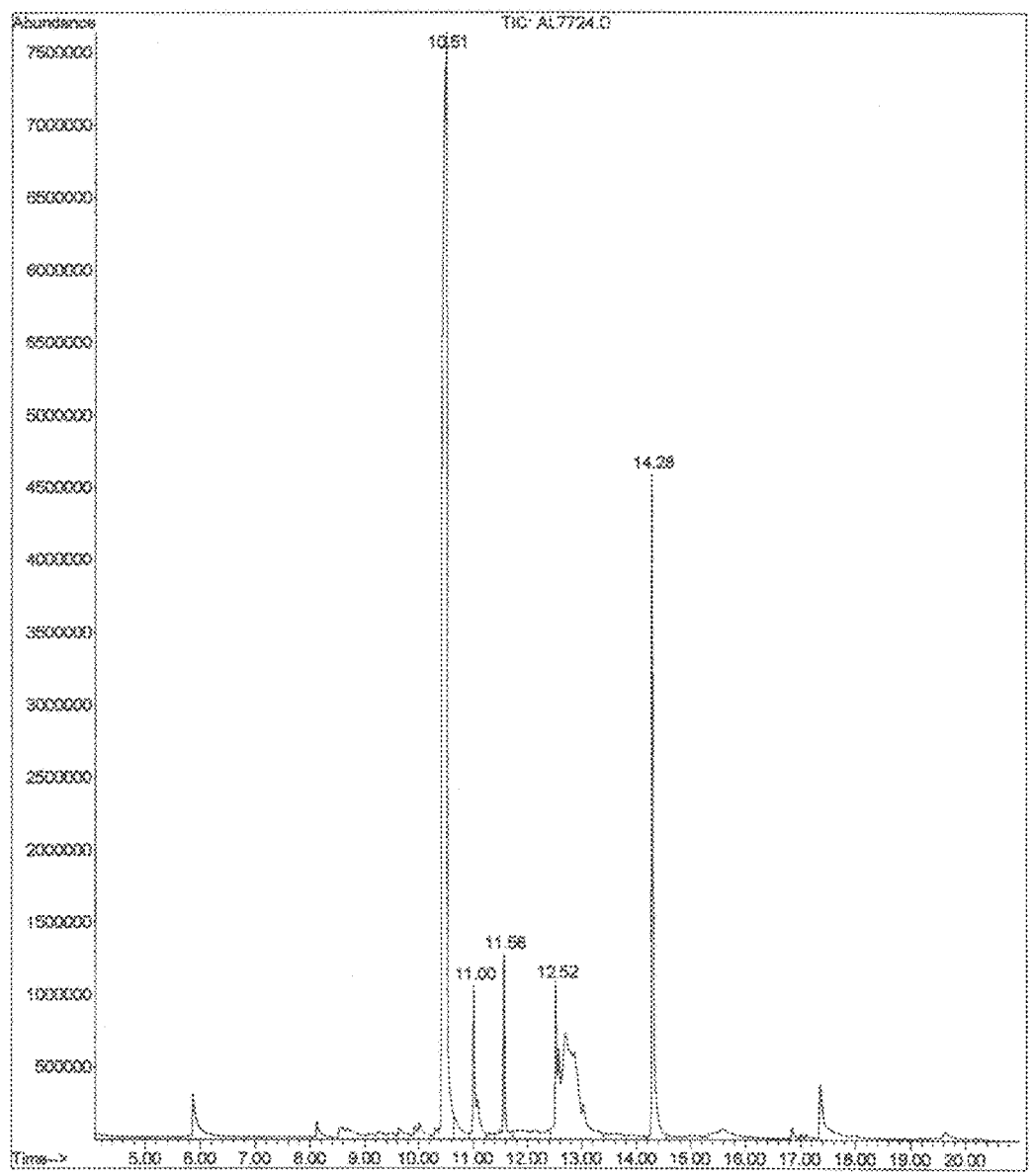
FIG. 5 is a graph showing a representative GC of the mixture in the reaction flask after RCM with Grubbs $1^{st}$ generation catalyst, according to embodiments of the invention.
Figure 6:
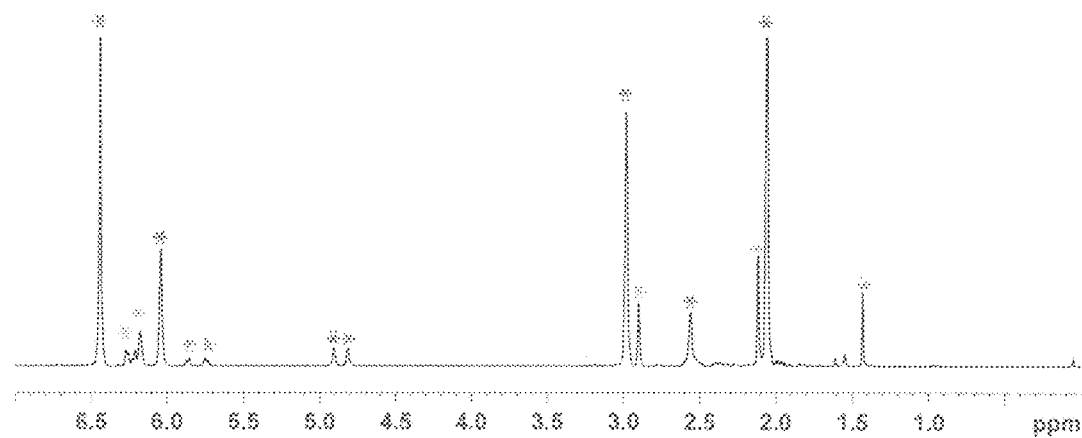
FIG. 6 is a graph showing a representative $^1H$ NMR of the 2-methylcyclopentadiene product from the RCM reaction, where minor products include 1-methylcyclopentadiene, methylcyclopentadiene dimer, and starting alcohols and ethers, according to embodiments of the invention.

Grubbs 1$^{st}$ generation catalyst (2) (26 mg, 0.1 mol %) was placed in a 25 mL round bottom flask charged with a Teflon stirbar. The flask was sealed with a septum and removed from the glove box. The flask was placed in an oil bath and held at 45° C. To this flask 5 mL of distilled linalool was added via syringe and the reaction was vented to an oil bubbler. Within 5 minutes slow bubbling was seen in the oil bubbler, but no bubbling was seen in the reaction flask. At 45 minutes bubbling began in the reaction flask and ceased completely at 90 min. $^1$H NMR showed 55% conversion of the starting linalool. FIG. 5. A representative QC of the mixture in the reaction flask after RCM with Grubbs 1$^{st}$ generation catalyst. Use peak with RT=10.51 represents unreacted linalool. Significant dehydration products are present with very little methylcyclopentenol (RT ~6 min) present.

EXAMPLE 3

RCM with 2$^{nd}$ Generation Grubbs (3)

2$^{nd}$ generation Grubbs catalyst (3) (12 mg, 0.1 mol %) was placed in a 25 mL round bottom flask charged with a Teflon stirbar. The flask was sealed with a septum and removed from the glove box. The flask was placed in an oil bath and held at 60° C. To this flask, 3 mL of distilled linalool was added via syringe and the reaction was vented to an oil bubbler. Within 5 minutes bubbling was seen in the flask and this continued for 20 minutes after which bubbling ceased. $^1$H NMR taken at 30 min showed 36% conversion of the starting linalool. A spectrum at 3 h showed no further conversion.

EXAMPLE 4

Dehydration Catalyst Screening

Unless otherwise noted all of the dehydration test reactions were carried out at room temperature with stirring in air. The dehydrating agent was added to 1 mL of 1 in a vial and stirred. Crude products were analyzed by $^1$H NMR and GC-MS.

Nafion SAC-13: 50 mg of Nafion Sac-13 was added and the reaction was stirred for 1 h. $^1$H NMR showed only a small amount of the starting alcohol and no methylcyclopentadiene. Analysis by GC-MS gave 6% 1, 35% ethers, 23% dimers, 28% trimers and 9% tetramers.

MMT-K10: 50 mg of MMT-K10 was added and the reaction was stirred for 1 h. $^1$H NMR showed only a small amount of the starting alcohol and no methylcyclopentadiene. Analysis by GC-MS gave 5% 1, 41% ethers, 22% dimers, 28% trimers and 4% tetramers.

HCl: 1 mL of 2M HCl was added and the reaction was stirred for 1 hour. $^1$H NMR at 1 h showed no starting alcohol and no methylcyclopentadiene. Analysis by GC-MS gave a complex mixture of ethers, and dimers making up 86% of the sample with an additional 12% trimers and 1% tetramers.

Benzoic Acid: 50 mg of benzoic acid was added and the reaction was stirred for 1 hour. The NMR showed no reaction at 1 hour and the solution was left to stir overnight. $^1$H NMR at 20 h showed only a small amount of the starting alcohol, and no methylcyclopentadiene. Analysis by GC-MS gave 8% 1, 66% ethers, 22% dimers and 4% trimers.

Magnesium Sulfate: 150 mg of MgSO$_4$ was added and the reaction was stirred for 1 h. $^1$H NMR showed no reaction and the mixture was left to stir overnight. $^1$H NMR at 24 h showed significant amounts of the starting alcohol, and no methylcyclopentadiene: the reaction was stopped at this point. Analysis by GC-MS gave 16% 1 and 84% ethers. No conversion to methylcyclopentadiene or heavier products was observed.

Pd(COD)Cl$_2$: 50 mg of Pd(COD)Cl$_2$ was added and the reaction was stirred for 1 h; $^1$H NMR taken at this point showed no significant conversion and the solution was left to stir overnight. $^1$H NMR at 24 hours showed no starting alcohol, and no methylcyclopentadiene. Analysis by GC-MS gave <1% 1, 14% ethers, 66% dimers, 16% trimers, and 7% tetramer.

Aluminum Phosphate with 4Å Mol. Sieves: 310 mg of AlPO$_4$ and 500 mg of 4Å molecular sieves were added. This flask was placed in a 60° C. oil bath and 6 mL of 1 was added via syringe. The desired methylcyclopentadiene was obtained through distillation under vacuum (~40 torr). The receiving flask was placed in dry ice to ensure no loss of product. The reaction ran for 8 hours and only ~100 μL was collected in the receiving flask. $^1$H NMR of this portion showed a mixture of 1-methylcyclopentadiene and 2-methylcyclopentadiene in a 1:3 ratio, respectively. The reaction flask was a thick orange oil and was not analyzed further.

EXAMPLE 5

Preparation of AlPO$_4$

This synthesis was adapted from a literature procedure. Aluminum nitrate nonahydrate, Al(NO$_3$)$_3$·9H$_2$O (16.0 g, 43 mmol) was dissolved in 75 mL of DI water. 3 mL of 85% H$_3$PO$_4$ was added dropwise with rapid stirring. 13 mL of 27% NH$_4$OH was diluted in 30 mL of DI water and then this diluted solution was slowly added dropwise to the reaction mixture. Once addition was complete a thick white precipitate had formed and an additional 20 mL of DI water was added to allow for continued stirring of the mixture. The slurry was left to stir for 20 hours after which time the solution was filtered. The resulting solid was re-dispersed in 100 mL of DI water and stirred for 1 hour. The mixture was then centrifuged and the water was decanted. The solid was dried overnight at 120° C. in a vacuum oven. The white solid was powdered using a mortar and pestle to yield 4.78 g of white solid.

EXAMPLE 6

Dehydration with AlPO$_4$ & MgSO$_4$

AlPO$_4$ (1.34 g, 11 mmol) and MgSO$_4$ (1.63 g, 13 mmol) were placed in a 50 mL round bottom flask charged with a stirbar. To this flask 1 (13.01 g, 0.13 mol) was added, and the flask was fit with a small distillation head. The receiving flask was placed in a dry ice bath and the reaction was placed under vacuum (40 torr). The reaction was run at 60° C. for 5 hours. Total yield of the distillate was 78%. $^1$H NMR for the major product, 2-methylcyclopentadiene (CDCl$_3$) δ: 2.06 (s, 3H), 2.98 (s, 1H), 6.04 (s, 1H), 6.44 (s, 2H).

Figure 7:
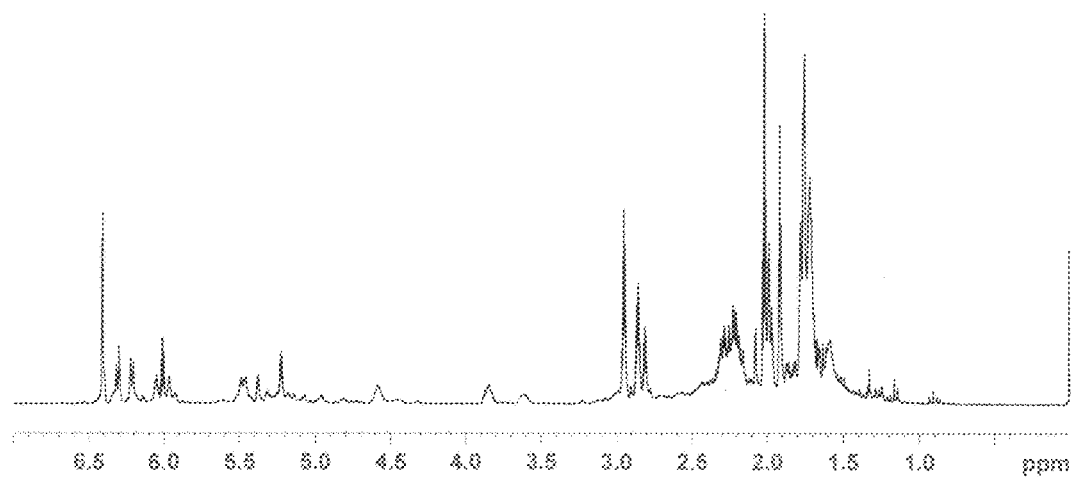
FIG. 7 is a graph showing a representative $^1H$ NMR spectrum of the dehydration of 1 with the heterogeneous acid catalyst, Nafion SAC-13, according to embodiments of the invention.
Figure 8:
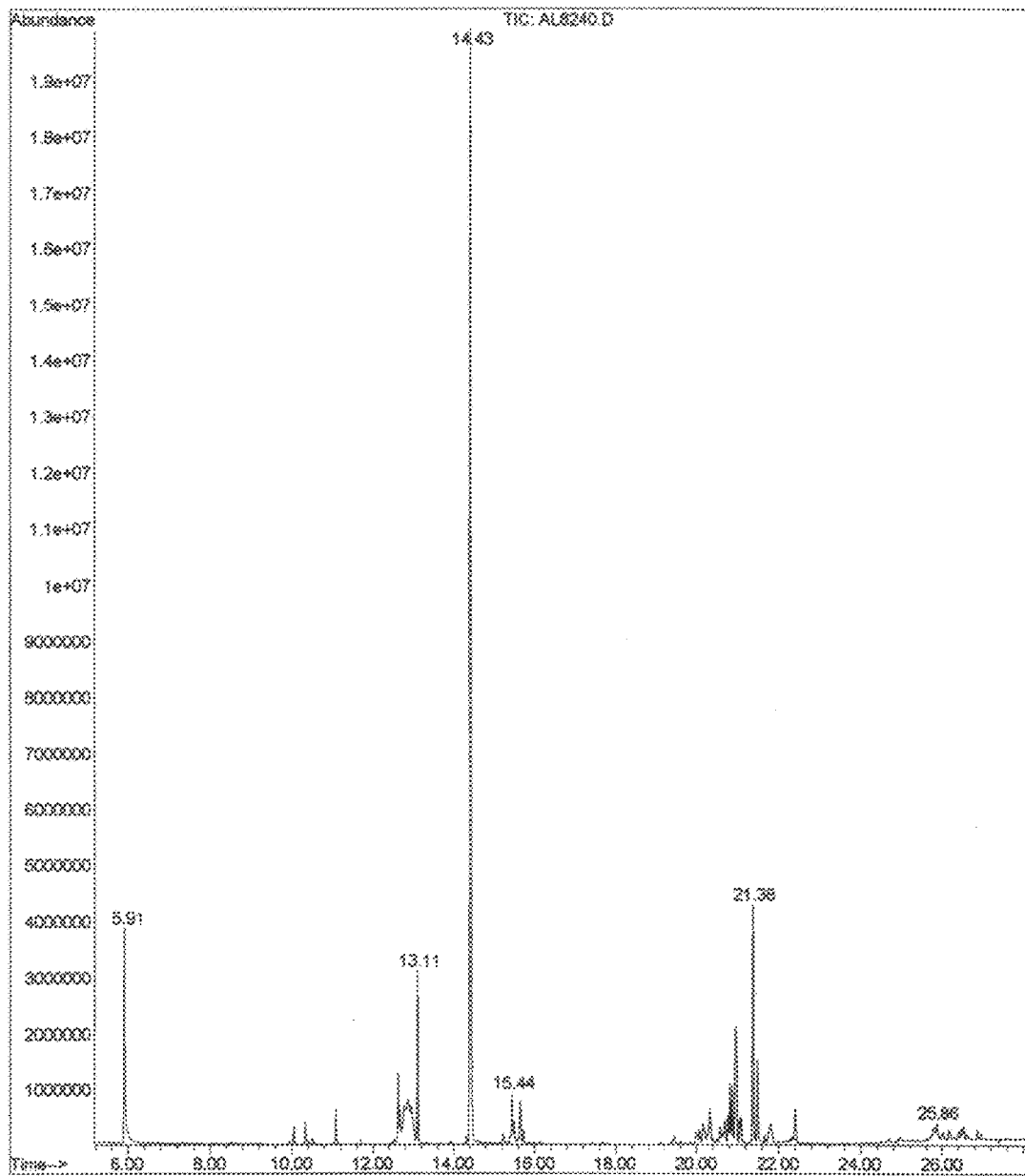
FIG. 8 is a graph showing a representative GC from the reaction flask after dehydration with Nafion SAC-13 shows starting material, ethers, dimers, miners, and tetramers in solution, according to embodiments of the invention.
Figure 9:
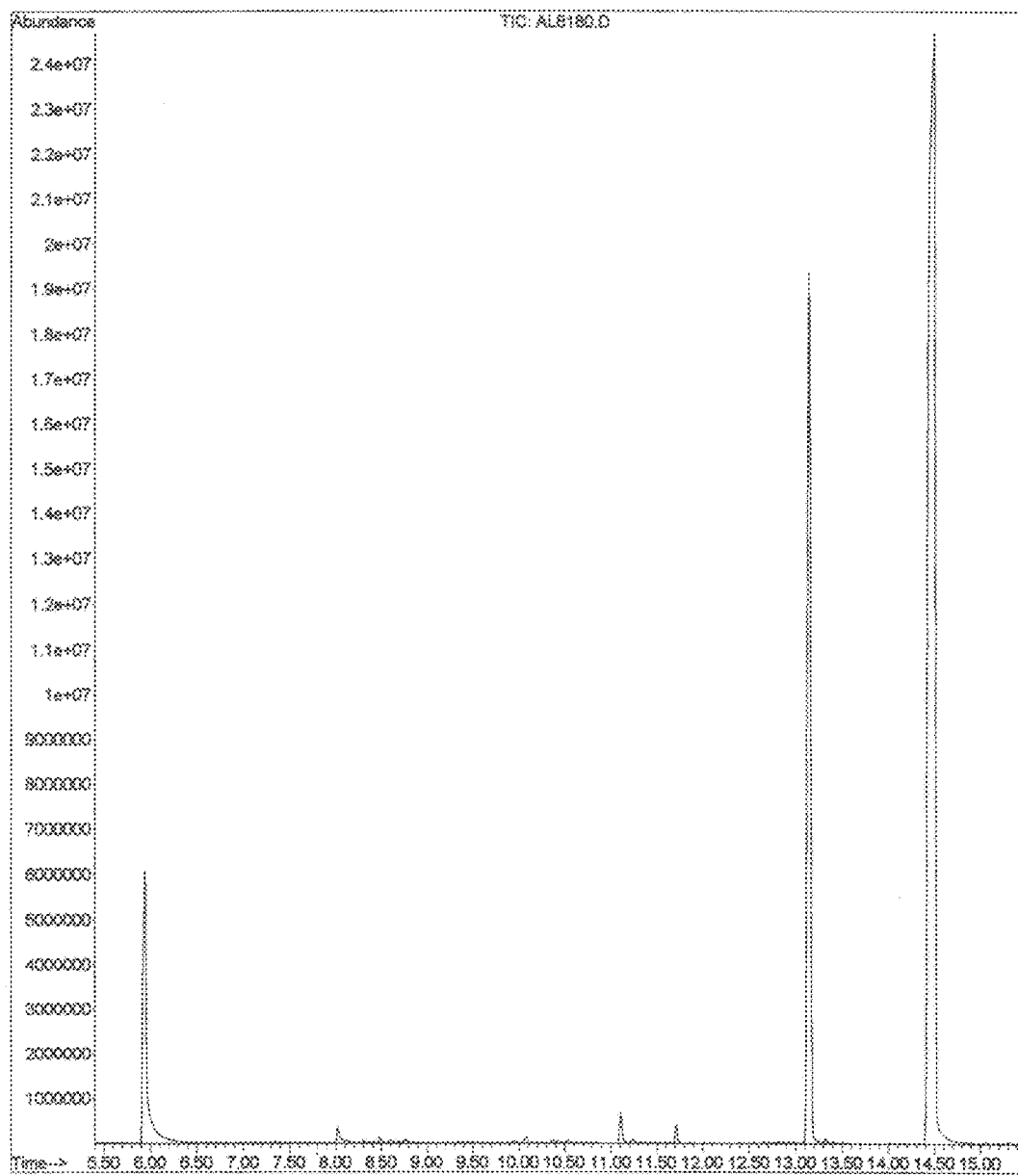
FIG. 9 is a graph showing a representative GC from the reaction flask after dehydration with $AlPO_4$, according to embodiments of the invention.

FIG. 5. Representative $^1$H NMR of the 2-methylcyclopentadiene product from the RCM reaction, minor products include 1-methylcyclopentadiene, methyl cyclopentadiene dimer, and starting alcohols and ethers. FIG. 7. A representative $^1$H NMR spectrum of the dehydration of 1 with the heterogeneous acid catalyst, Nafion SAC-13. FIG. 8. A representative GC from the reaction flask after dehydration with Nafion SAC-13 shows starting material, ethers, dimers, trimers, and tetramers in solution. FIG. 9. A representative GC from the reaction flask after dehydration with AlPO$_4$. The only major peaks observed are for starting material and ethers; no heavier product formation is observed.

EXAMPLE 7

Figure 10:
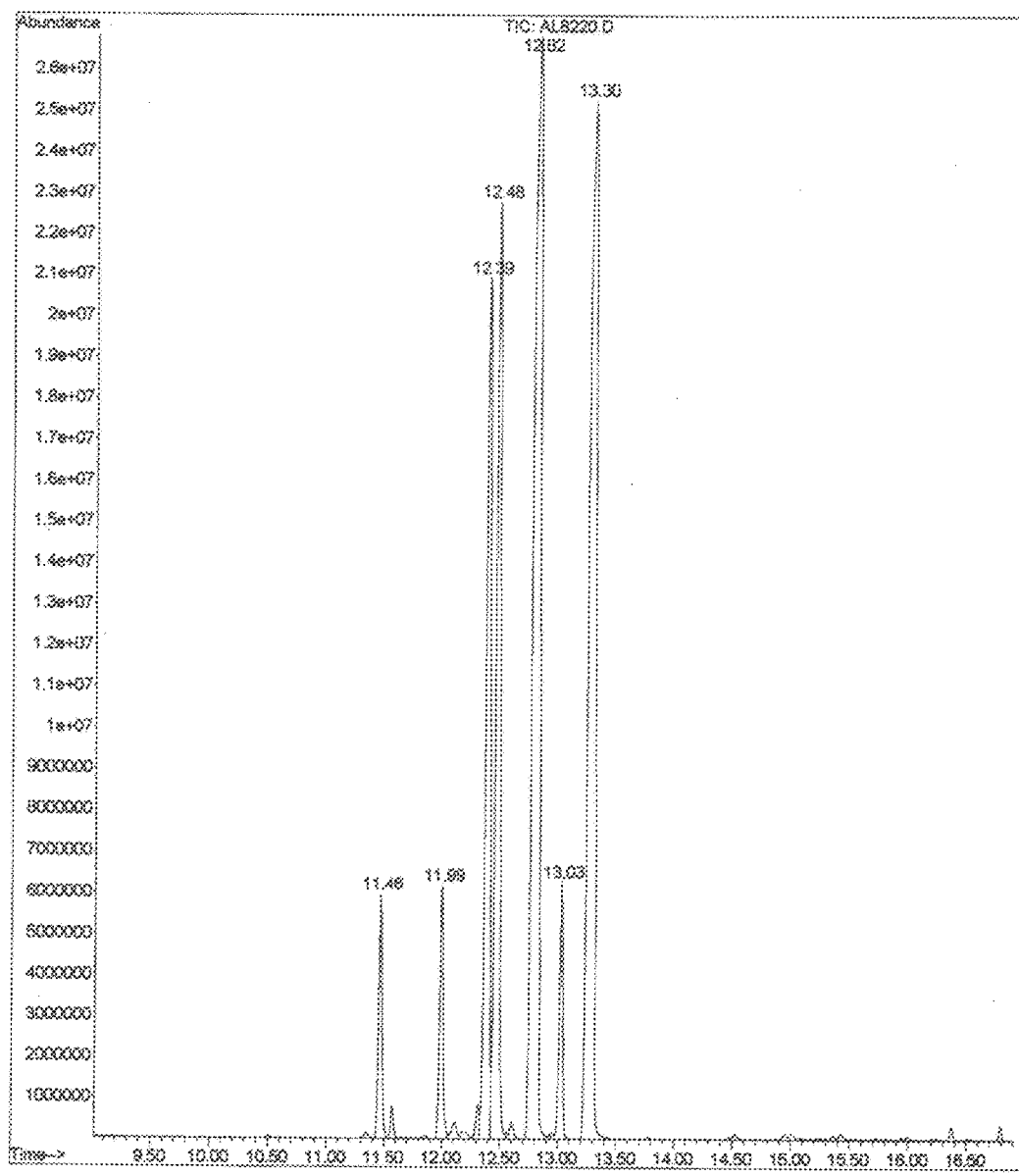
FIG. 10 is a graph showing a GC of the dimer mixture after hydrogenation with $PtO_2$ at 40 psi $H_2$, according to embodiments of the invention.

Hydrogenation of MCPD Dimers 8 g (0.1 mol) of MCPD dimers were diluted with 20 mL THF. PtO$_2$ (80 mg, 0.35 mmol) was added to the mixture which was then transferred to a small Parr hydrogenation apparatus under 40 psi H$_2$ with shaking. The pressure was monitored and hold between 30-40 psi for the duration of the reaction. After 20 hours H$_2$ was no longer being consumed and the reaction was stopped. The excess H$_2$ was removed under reduced pressure and the platinum catalyst was removed by filtration through a plug of glass wool. THF was removed under reduced pressure to yield a mixture of hydrogenated MCPD dimers which were subsequently analyzed by GC-MS. FIG. 10. GC of the dimer mixture after hydrogenation with PtO$_2$ at 40 psi H$_2$.

Other sesquiterpenes are examples of isoprenoid feedstocks that are embodiments of the invention. The invention generally relates to the conversion of sesquiterpenes to high density fuels.

The biosynthesis of farnesene and use as a standalone diesel/jet fuel or component of same is covered in the following USPTO applications: 20090272352, 20090272119, 20090020090, 20090020089, and 20080092829. Farnesane, the reduced form of farnesene, is a linear sesquiterpene of relatively low density (0.766 g/mL).

High density fuels have applications in a variety of Navy platforms including jet aircraft, ships, missiles, and UAVs. The fuels developed herein will help to meet Navy goals focused on the use of renewable and sustainable fuels while providing improved performance over conventional, petroleum-based fuels.

Embodiments of this invention describe the conversion of sesquiterpenes to high density fuels. The sesquiterpenes can be either extracted from plants or specifically produced by bioengineered organisms from waste biomass. This approach allows for the synthesis of high performance renewable fuels.

Embodiments of the invention detail processes for conversion of sesquiterpenes to high density fuel mixtures. Aspects of the process include hydrogenation of the sesquiterpenes to improve stability of the fuels as well as selective isomerization of the sesquiterpenes to improve density, net heat of combustion, low temperature viscosity, and cetane number. The isomerization process can be carried out with heterogeneous catalysts at moderate temperatures and requires no solvent. Thus, embodiments of the invention provide a route for the sustainable production of renewable, ultra-performance fuels.

The general procedure for synthesizing high density sesquiterpene fuels is as follows:

1. A pure sesquiterpene or mixture of sesquiterpenes are either extracted from plant sources (e.g. clove oil) or 2. a) A biomass source (including lignocellulosic, cellulosic, or hemicellulosic feedstocks) is hydrolyzed to produce a sugar solution.

b) The sugar solution is fermented to a sesquiterpene or mixture of sesquiterpenes by a bioengineered organism.

3. The hydrocarbons are purified by solvent extraction, pervaporation, membrane separation, or distillation.

4. Pure sesquiterpenes or mixtures are then:

a) Directly hydrogenated and distilled to yield a liquid fuel or b) Isomerized with heterogeneous acidic catalysts to produce a pure compound or complex mixture of hydrocarbons which is then hydrogenated and distilled to yield a liquid fuel.

Process:

1. A pure sesquiterpene or mixture of sesquiterpenes is isolated from a plant source. This can be accomplished by steam distillation, solvent extraction, or pyrolysis, among other techniques.

2a. In an alternate approach, biomass can be hydrolyzed to produce a sugar solution. This step can be accomplished by physical, chemical, or enzymatic methods, or any combination thereof.

2b. The sugar solution is used as a food source for bioengineered organisms that produce sesquiterpenes in either a batch or continuous mode.

3. Regardless of the source, the sesquiterpenes can be upgraded through techniques including fractional distillation, chemical treatments, and extractions to produce a suitably pure hydrocarbon feedstock composed of either a single sesquiterpene or complex mixture of sesquiterpenes. In the case of the biosynthesized sesquiterpenes (2b), the major impurity is water which can be effectively removed by both membrane separation techniques as well as by distillation.

4a) Sesquiterpenes are directly hydrogenated to produce a high density fuel. Catalysts based on Ni, Pd, Pt, Cu, and Ru can be utilized under moderate hydrogen pressures.

Figure 11:
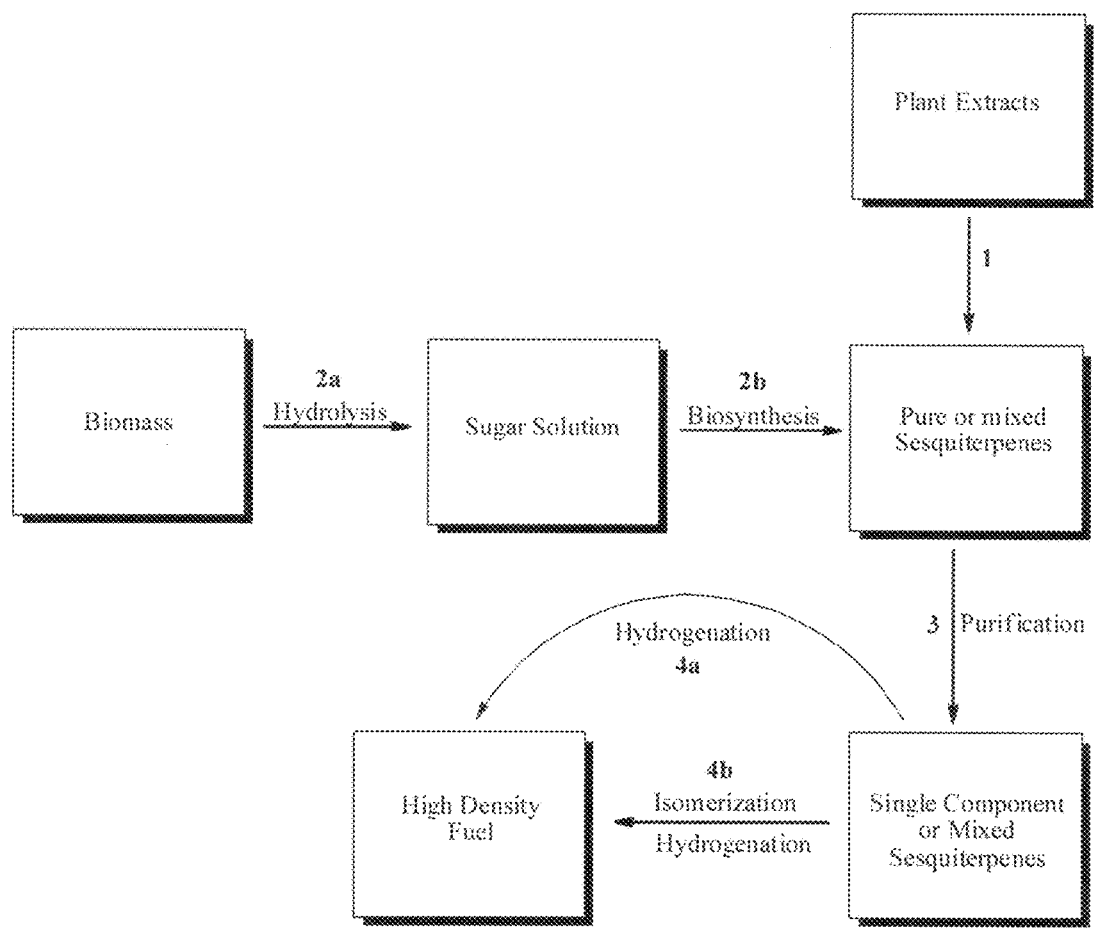
FIG. 11 is a block diagram illustrating the steps to produce high density biofuels from sesquiterpenes, according to embodiments of the invention.

4b) To improve specific fuel properties such as viscosity, net heat of combustion, density, and cetane number, sesquiterpenes can be readily isomerized with heterogeneous acid catalysts including, but not limited to; Nafion, Amberlyst, Montmorillonite K-10, zeolites and supported polyphosphoric acid. Sesquiterpenes can also be effectively isomerized with Lewis acids and mineral acids. After isomerization, these sesquiterpenes can be hydrogenated as in 4a. Pure sesquiterpenes or defined mixtures of sesquiterpenes can be isolated by fractional distillation to generate fuels with specific properties. FIG. 11 is a block diagram overview showing the steps of the embodiments of the invention therein.

Example 1 (high catalyst loading). 50 mL of caryophyllene (technical grade) is combined with 500 mg of Nafion SAC-13 in a flask. The mixture is vigorously stirred and heated to 100° C. overnight. The pale yellow solution is decanted, hydrogenated at 50 psig H$_2$ with 50 mg PtO$_2$ as catalyst. The resulting mixture is filtered and vacuum distilled to yield a colorless fuel mixture containing saturated hydrocarbons derived from seven main isomers including α-neoclovene, clovene, and α-panasinsene (see Scheme 7).

Scheme 7. Products resulting from the acid-catalyzed isomerization of β-caryophyllene. Numbers under the structures represent the weight percentage of each molecule. The first number results from low catalyst loading, while the number in parentheses results from high catalyst loading as described in the process.

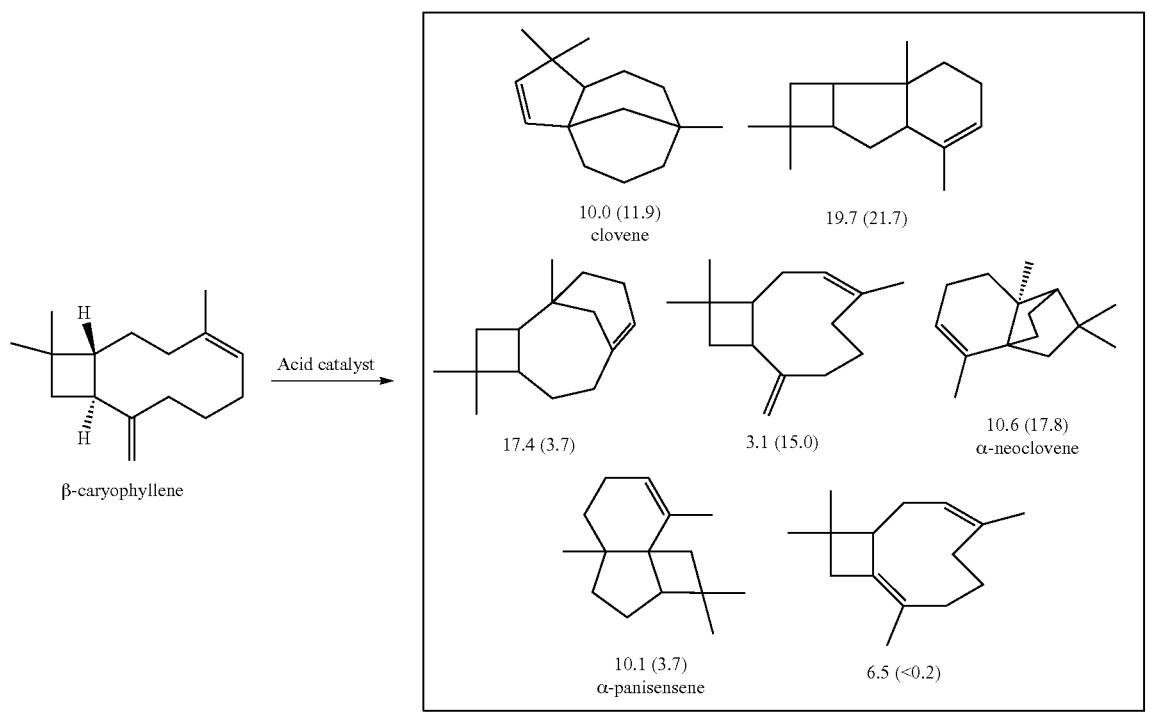

Example 2 (low catalyst loading). 500 mL of caryophyllene is combined with 2 g of Nafion SAC-13 in a flask and subjected to the same conditions as in Example 1. A significantly different product distribution results (see Scheme 8).

Example 3. 175 mL of valencene (Scheme 9) biosynthesized from sucrose is hydrogenated at 50 psig $H_2$ with 100 mg $PtO_2$ as catalyst. After hydrogenation the catalyst flocculates and the catalyst is separated by decantation. The properties of this fuel mixture are listed in Table 3.

Example 4. 175 mL of premnaspirodiene (Scheme 9) biosynthesized from sucrose is hydrogenated as in Example 3. The properties are listed in Table 3.

Example 5. 175 mL of commercial caryophyllene (technical grade) is hydrogenated as in Example 3. The properties are listed in Table 3.

Example 6. 5 g of valencene biosynthesized from sucrose are combined with 0.1 g of Nafion SAC-13 and the mixture is stirred and heated to 100° C. for 16 h. The solution is decanted to yield a mixture of isomers.

Example 7. 5 g of premnaspirodiene biosynthesized from sucrose is isomerized as described in Example 6.

TABLE 3

Key Properties of Sesquiterpene Fuels.
Table 3. Key Properties of Sesquiterpene Fuels

| Sesquiterpene | Density (g/mL) | NHOC (btu/gal) | 40° C. Viscosity (cSt) | −20° C. Viscosity (cSt) | Ignition Delay (ms) | Derived Cetane No. |
|---|---|---|---|---|---|---|
| Valencane | 0.879 | 135,386 | 4.417 | 50.24 | 10.562 | 23.26 |
| Caryophyllane | 0.85 | 132,790 | 4.067 | 60.47 | 9.75 | 24.52 |
| Premnaspirodiane | 0.882 | 135,564 | 3.812 | 42.91 | 7.779 | 28.65 |
| HDCL-8 | 0.90 | 137,800 | 53.58 | NM | 13.173 | 20.23 |
| HDCL-9 | 0.90 | 137,100 | 5.07 | 61.96 | 6.549 | 32.53 |
| HDCL-10 | 0.92 | 140,900 | NM | NM | NM | NM |

Note:
HDCL-8 is the fuel generated from caryophyllene with high catalyst loading, HDCL-9 is the fuel generated with low catalyst loading. The density and net heat of combustion of HDCL-10 has been calculated based on a distillate cut containing primarily high-density components (i.e. clovene/neoclovene and assuming a density of 0.92 g/mL).

Scheme 8. Isomerization of caryophyllene with a heterogeneous acid catalyst.

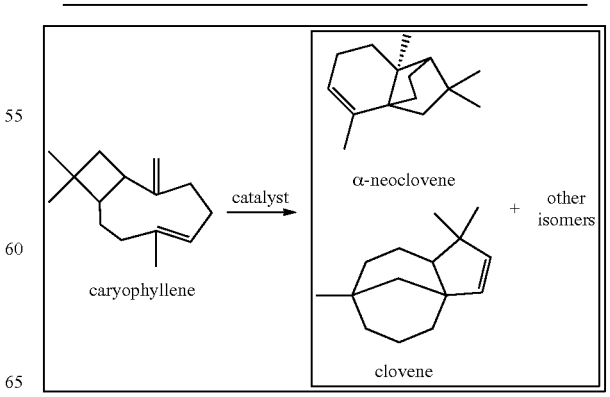

Scheme 9. Structures of valencene and premnaspirodiene

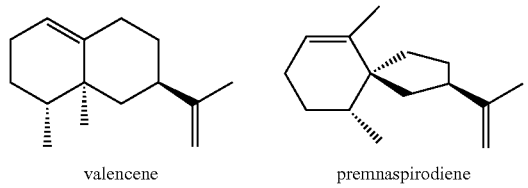

valencene    premnaspirodiene

Embodiments of the invention generally relate to methods for manufacturing jet and diesel fuels including, providing pure and/or mixed sesquiterpenes isolated from plant extracts and/or biosynthesized from biomass, purifying the pure and/or mixed sesquiterpenes to produce single components or mixtures of sesquiterpenes, converting the single component or mixed sesquiterpenes by either, directly hydrogenating the single component or mixed sesquiterpenes with at least one hydrogenation catalyst under hydrogen pressure, or isomerizing either with or without a solvent, the single component or mixed sesquiterpenes with at least one heterogeneous acid catalyst to produce isomers and hydrogenating the isomers with at least one hydrogenation catalyst under hydrogen pressure, and distilling either the hydrogenated single component or mixed sesquiterpenes or the hydrogenated isomers to produce high density fuels.

Another aspect of the invention generally relates to the production and blends of fuels. In embodiments, the pure and/or mixed sesquiterpenes are selected from the group consisting of valencene, premnaspirodiene, caryophyllene, humulene, clovene, neoclovene, panasinsene, thujopsene, longifolene, cubebene, zizaene, santalene, longipinene, isomers of the above sesquiterpenes, other cyclic terpenes, and any mixtures thereof. In embodiments, the single component or mixed sesquiterpenes are selected from the group consisting of caryophyllene, valencene, premnaspirodene, or any mixture thereof. In embodiments, the isomers are at least one isomer selected from the group consisting of α-neoclovene, clovene, or any mixture thereof. In embodiments, the hydrogenating catalyst having at least tine metal selected from the group consisting of Ni, Cu, Pd, Pt, $PtO_2$, Ru and the reaction is conducted without a solvent.

In embodiments, the heterogeneous acid catalyst are selected from the group consisting of at least one of Nafion (perfluorinated sulfonic acid resins). Amberlyst (cross-linked sulfonic acid resins). Montmorillonite K-10, zeolites, polyphosphoric acids, cation exchange resins, Lewis acid catalysts, supported Bronsted acid catalysts, mineral acids including $H_2SO_4$ and $H_3PO_4$, and any mixtures thereof. In embodiments, the plant extracts are selected from the group consisting of clove oil or any essential oil having significant quantities of cyclic sesquiterpenes, and mixtures of said oils. In embodiments, the biomass includes at least one of sucrose, glucose, fructose, cellobiose, other reducing sugars, cellulose, and hemicelluloses in any proportion.

Another aspect of the invention generally relate to methods for manufacturing jet and diesel fuels including, providing pure and/or mixed sesquiterpenes isolated from plant extracts and/or biosynthesized from biomass, purifying the pure and/or mixed sesquiterpenes to produce single components or mixtures of sesquiterpenes producing a first set of fuels, or converting the single component or mixed sesquiterpenes by isomerizing either with or without a solvent, the single component or mixed sesquiterpenes with at least one heterogeneous acid catalyst to produce isomers, and distilling the isomers producing a second set of fuels. All blends of fuels are incorporated into all aspects of the invention.

Yet other aspects of the invention generally relate to a first set of fuels produced from the methods above. Still yet other aspects of the invention generally relate to a second set of fuels produced from the methods above.

In embodiments, the fuels are pure sesquiterpanes or prepared by selective fractional distillation of sesquiterpane mixtures (density >0.90 g/mL, NHOC>137,000 btu/gal). In other embodiments, the diesel fuels are pure sesquiterpanes or generated by selective fractional distillation of sesquiterpane mixtures (cetane number >30). In yet other embodiments, the diesel fuels are generated by blending sesquiterpane mixtures with known cetane enhancers or antioxidants for fuels. In embodiments, the fuels generated by blending sesquiterpene fuels with petroleum-based fuels including JP-10, RJ-4, JP-8, JP-5, F-76, Diesel #2, Jet A, and any renewable fuel.

In embodiments, the high density missile-turbine fuels are blends of cyclic sesquiterpanes with JP-10 in a desired proportion. In embodiments, the high density jet fuels are blends of cyclic sesquiterpanes with jet fuels including JP-5, JP-8, and Jet A. In embodiments, the high density diesel fuels are blends of cyclic sesquiterpanes with petroleum-derived diesel fuel. In embodiments, the high density jet/diesel fuels are blends of cyclic sesquiterpanes with fuels generated by ethylene oligomerization. In embodiments, the high density jet/diesel fuels are blends of cyclic sesquiterpanes with fuels generated by butene oligomerization. In embodiments, the high density jet/diesel fuels are blends of cyclic sesquiterpanes with fuels generated by hexene oligomerization. In embodiments, the high density jet/diesel fuels are blends of cyclic sesquiterpanes with diesel fuels produced from natural gas.

Prophetic examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for making a blended fuel comprising a hydrogenated Diels-Alder cycloaddition adduct, comprising
providing a feedstock comprising a linear sesquiterpene;
producing a first mixture by metathesizing said feedstock from about 1 hour to about 24 hours using a metathesis catalyst at a temperature of from about 0° C. to about 150° C. under an inert-gas atmosphere, wherein said metathesizing yields methylcyclopentadiene (MCPD) and at least one branched-chain hydrocarbon;

producing a second mixture by reacting said first mixture from about 0.3 hours to about 24 hours using a first acidic catalyst at a temperature of from about 15° C. to about 350° C., wherein said reacting yields at least one Diels-Alder cyclo-addition adduct;

producing a third mixture by removing from said second mixture said first acidic catalyst;

producing a fourth mixture by hydrogenating said third mixture from about 1 hour to about 24 hours with hydrogen gas at pressures ranging from about 1 atm to about 100 atm using a hydrogenation catalyst at a temperature of from about 0° C. to about 250° C. yielding a hydrogenated C9 hydrocarbon and at least one hydrogenated Diels-Alder cyclo-addition adduct, and distilling the hydrogenated C9 hydrocarbon and the at least one hydrogenated Diels-Alder cyclo-addition adduct to isolate the at least one hydrogenated Diels-Alder cycloaddition adduct, wherein said fourth mixture comprises the hydrogenated C9 hydrocarbon producing a fifth mixture by isomerizing said fourth mixture from about 0.3 hours to about 48 hours using a second acidic catalyst at temperatures ranging from about 15° C. to about 350° C. under an inert-gas atmosphere, wherein said isomerizing yields at least one alkyl-adamantane; and blending the at least one hydrogenated Diels-Alder cycloaddition adduct with a petroleum-based fuel to produce said blended fuel comprising a hydrogenated Diels-Alder cycloaddition adduct.

2. The method according to claim 1, wherein said metathesis catalyst further comprises a homogeneous transition metal catalyst with the transition metal selected from the group consisting of ruthenium, molybdenum, tungsten, rhenium, titanium, and any combination thereof.

3. The method according to claim 1, wherein said metathesis catalyst further comprises a heterogeneous solid having a transition metal compound selected from the group consisting of ruthenium, molybdenum, tungsten, rhenium, and titanium on at least one solid supporting material selected from the group consisting of zeolites, silica, alumina, aluminosilicates, zirconia, titania, metal oxides, activated carbon, carbon supports, cross-linked polystyrene, macroreticular resins, and polymer-based supports.

4. The method according to claim 1, wherein said producing said first mixture by said metathesizing further comprises distilling said MCPD and said at least one branched-chain hydrocarbon to remove and isolate said MCPD, wherein said first mixture comprises said at least one branched-chain hydrocarbon.

5. The method according to claim 1, wherein said producing said first mixture by said metathesizing further comprises adding a high-boiling solvent selected from the group consisting of decalin, xylene, and other non-protic solvents with a boiling temperature at standard conditions ranging from about 100° C. to about 200° C.

6. The method according to claim 1, wherein said producing said second mixture by said reacting further comprises adding at least one conjugated diene reagent selected from the group consisting of cyclopentadiene, methylcyclopentadiene, terpinene, cyclic conjugated dienes, butadiene, isoprene, and conjugated dienes.

7. The method according to claim 1, wherein said first acidic catalyst further comprises a homogeneous Lewis acid.

8. The method according to claim 1, wherein said first acidic catalyst further comprises a heterogeneous Lewis acid supported on at least one solid material selected from the group consisting of acidic zeolites, aluminosilicates, alumina, zirconia, titania, acidic silica, acidic clays, acidic metal oxides, cross-linked sulfonated polystyrene, macroreticular resins, polymers, crosslinked ionic liquids, crosslinked poly(ionic liquids), crosslinked ionic liquid gels, and any combination thereof.

9. The method according to claim 1, wherein said hydrogenation catalyst further comprises a transition-metal selected from the group consisting of nickel, palladium, platinum, ruthenium, copper, and any combination thereof.

10. The method according to claim 1, wherein said producing said fourth mixture by said hydrogenating further comprises the addition of at least one polar solvent selected from the group consisting of ethyl acetate, organic esters, acetic acid, organic acids, methanol, ethanol, alcohols, tetrahydrofuran, dioxane, ethers, and any combination thereof.

11. The method according to claim 1, wherein said second acidic catalyst further comprises a homogeneous Lewis acid selected from the group consisting of $AlCl_3$, $FeCl_3$, $TiCl_4$, $ZnCl_2$, $SbF_5$, $BF_3$, a homogeneous Lewis-acid compound, and any combination thereof, wherein the homogeneous Lewis-acid compound is derived from Ti, V, Cr, Mn, Fe, Co, Ni, Cu, Zn, B, Al, Sn, Sb, and any combination thereof.

12. The method according to claim 1, wherein said second acidic catalyst further comprises at least one ionic liquid selected from the group consisting of pyridinium-derived ionic liquids, imidazolium derived ionic liquids, acidic ionic liquids, acidic chloroaluminate ionic liquids, clay-supported chloroaluminate ionic liquids, [1-butyl-3-methylimidazolium][bis(trifluoromethylsulfonylimide)], [1-butyl-3-methylimidazolium][tricyanomethanide], [tri(butyl)(tridecyl)phosphonium][bis(trifluoromethylsulfonylimide)], triethylammonium chloroaluminate, [1-butyl-3-methylpyridinium] chloroaluminate, [1-butyl-3-methylimidazolium] chloroaluminate, and any combination thereof.

13. The method according to claim 1, wherein said second acidic catalyst further comprises a heterogeneous Lewis acid selected from the group consisting of $AlCl_3$, $FeCl_3$, $TiCl_4$, $ZnCl_2$, $SbF_5$, $BF_3$, and a Lewis acid based on transition metals including Ti, V, Cr, Mn, Fe, Co, Ni, Zn, B, Al, Sn, Sb, and wherein said heterogeneous Lewis acid is supported on at least one solid material selected from the group consisting of zeolites, aluminosilicates, alumina, zirconia, titania, silica, clays, metal oxides, cross-linked sulfonated polystyrene, macroreticular resins, polymers, crosslinked ionic liquids, crosslinked poly(ionic liquids), crosslinked ionic liquid gels, and any combination thereof.

14. The method according to claim 1, wherein said feedstock includes a component of the following formula:

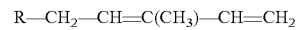

wherein R is selected from the group consisting of an alkyl, a cycloalkyl, a functionalized alkyl, an alkenyl, a functionalized alkenyl, an alkynyl, a functionalized alkynyl, an aromatic group, and a functionalized aromatic group.

* * * * *